(12) United States Patent
Kishkovich et al.

(10) Patent No.: US 6,296,806 B1
(45) Date of Patent: *Oct. 2, 2001

(54) PROTECTION OF SEMICONDUCTOR FABRICATION AND SIMILAR SENSITIVE PROCESSES

(75) Inventors: Oleg P. Kishkovich, Greenville; Devon A. Kinkead, Cumberland, both of RI (US)

(73) Assignee: Extraction Systems, Inc., Franklin, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/996,790

(22) Filed: Dec. 23, 1997

Related U.S. Application Data

(63) Continuation-in-part of application No. 08/795,949, filed on Feb. 28, 1997, now Pat. No. 6,096,267.

(51) Int. Cl.[7] .................................................. G01N 21/76
(52) U.S. Cl. .............................. 422/52; 422/62; 422/93; 436/111
(58) Field of Search ...................... 422/91, 93, 62, 422/52; 436/116, 111, 113, 172

(56) References Cited

U.S. PATENT DOCUMENTS

| | | | |
|---|---|---|---|
| 3,647,387 | 3/1972 | Benson et al. | 23/232 R |
| 3,727,029 | 4/1973 | Chrow | 219/301 |
| 3,787,184 | 1/1974 | Novak et al. | 23/230 R |
| 3,807,233 | 4/1974 | Crawford | 73/421 |
| 3,904,371 | 9/1975 | Neti et al. | 23/232 R |
| 3,911,413 | 10/1975 | Wallace | 340/237 R |
| 3,919,397 | 11/1975 | Gould | 423/405 |
| 3,967,933 | 7/1976 | Etess et al. | 23/232 |
| 3,996,008 | 12/1976 | Fine et al. | 23/254 R |
| 4,049,383 | 9/1977 | Burton et al. | 23/232 |
| 4,059,409 | 11/1977 | Barto et al. | 23/284 |
| 4,070,155 | 1/1978 | Fraim | 23/230 PC |
| 4,154,586 | 5/1979 | Jones et al. | 55/274 BN |
| 4,301,114 | 11/1981 | Roubehler et al. | 422/52 |
| 4,333,735 | 6/1982 | Hardy et al. | 23/232 R |
| 4,333,752 | 6/1982 | Thies et al. | 55/387 |
| 4,381,408 | 4/1983 | Roubehler et al. | 564/112 |

(List continued on next page.)

FOREIGN PATENT DOCUMENTS

| | | |
|---|---|---|
| 1201646 | 3/1986 | (CA) . |
| 214213 | 10/1984 | (DE) . |
| 58085155 | 5/1983 | (JP) . |
| 63-24149 | 5/1986 | (JP) . |
| 4-50756 | 2/1992 | (JP) . |
| 5-45289 | 2/1993 | (JP) . |
| 4-315048 | 3/1993 | (JP) . |
| 5-302895 | 11/1993 | (JP) . |
| 6-118077 | 4/1994 | (JP) . |

OTHER PUBLICATIONS

Viewgraph, "Compact Chemiluminescent $NO/NO_x$ Stack Gas Analyzer," Instrumatic International, received by one of the inventors on Nov. 21, 1997.

*Primary Examiner*—Jeffrey Snay
(74) *Attorney, Agent, or Firm*—Bowditch & Dewey, LLP

(57) ABSTRACT

A detection system for detecting base contamination at low concentrations in gas, for instance to protect a sensitive process, characterized in that the detection system is constructed to examine multiple amines in gas to produce a reading stoichiometrically related to the proton bonding characteristic of the multiple amines present, the detection system comprising at least two channels through which a gas to be examined passes, an amines remover located in one of the channels, at least one thermal/catalytic converter which discharges NO for each channel, and at least one chemiluminescent NO detector, whereby the total amine concentration is determined from the difference between the detected signals for the channels.

45 Claims, 18 Drawing Sheets

U.S. PATENT DOCUMENTS

| | | | |
|---|---|---|---|
| 4,473,282 | 9/1984 | Michlin | 354/300 |
| 4,530,272 | 7/1985 | Stokes | 96/34.5 |
| 4,701,306 | 10/1987 | Lawrence et al. | 422/101 |
| 4,714,482 | 12/1987 | Polak et al. | 55/158 |
| 4,726,824 | 2/1988 | Staten | 55/274 |
| 4,737,173 | 4/1988 | Kudirka et al. | 55/276 |
| 4,775,633 | 10/1988 | Roubehler et al. | 436/106 |
| 4,847,594 | 7/1989 | Stetter | 340/540 |
| 4,873,970 | 10/1989 | Freidank et al. | 128/202.22 |
| 4,890,136 | 12/1989 | Greene et al. | 355/27 |
| 4,921,651 | 5/1990 | Polak et al. | 264/41 |
| 4,946,480 | 8/1990 | Hanville | 55/270 |
| 5,009,678 | 4/1991 | Bikson et al. | 55/16 |
| 5,014,009 | 5/1991 | Arimoto et al. | 324/468 |
| 5,053,064 | 10/1991 | Hama et al. | 55/270 |
| 5,057,436 | 10/1991 | Ball | 436/113 |
| 5,061,296 | 10/1991 | Sengpiel et al. | 55/4 |
| 5,185,268 | 2/1993 | Bonometti et al. | 436/114 |
| 5,208,162 | 5/1993 | Osborne et al. | 436/6 |
| 5,288,306 | 2/1994 | Aibe et al. | 95/141 |
| 5,322,797 | 6/1994 | Mallow et al. | 436/106 |
| 5,325,705 | 7/1994 | Tom | 73/31.03 |
| 5,356,594 | 10/1994 | Neel et al. | 422/54 |
| 5,418,170 | 5/1995 | Roubehler et al. | 436/111 |
| 5,427,610 | 6/1995 | Croker | 95/114 |
| 5,434,644 | 7/1995 | Kitano et al. | 355/30 |
| 5,567,623 | 10/1996 | Roubehler et al. | 436/158 |
| 5,582,865 | 12/1996 | Rezuke et al. | 427/244 |

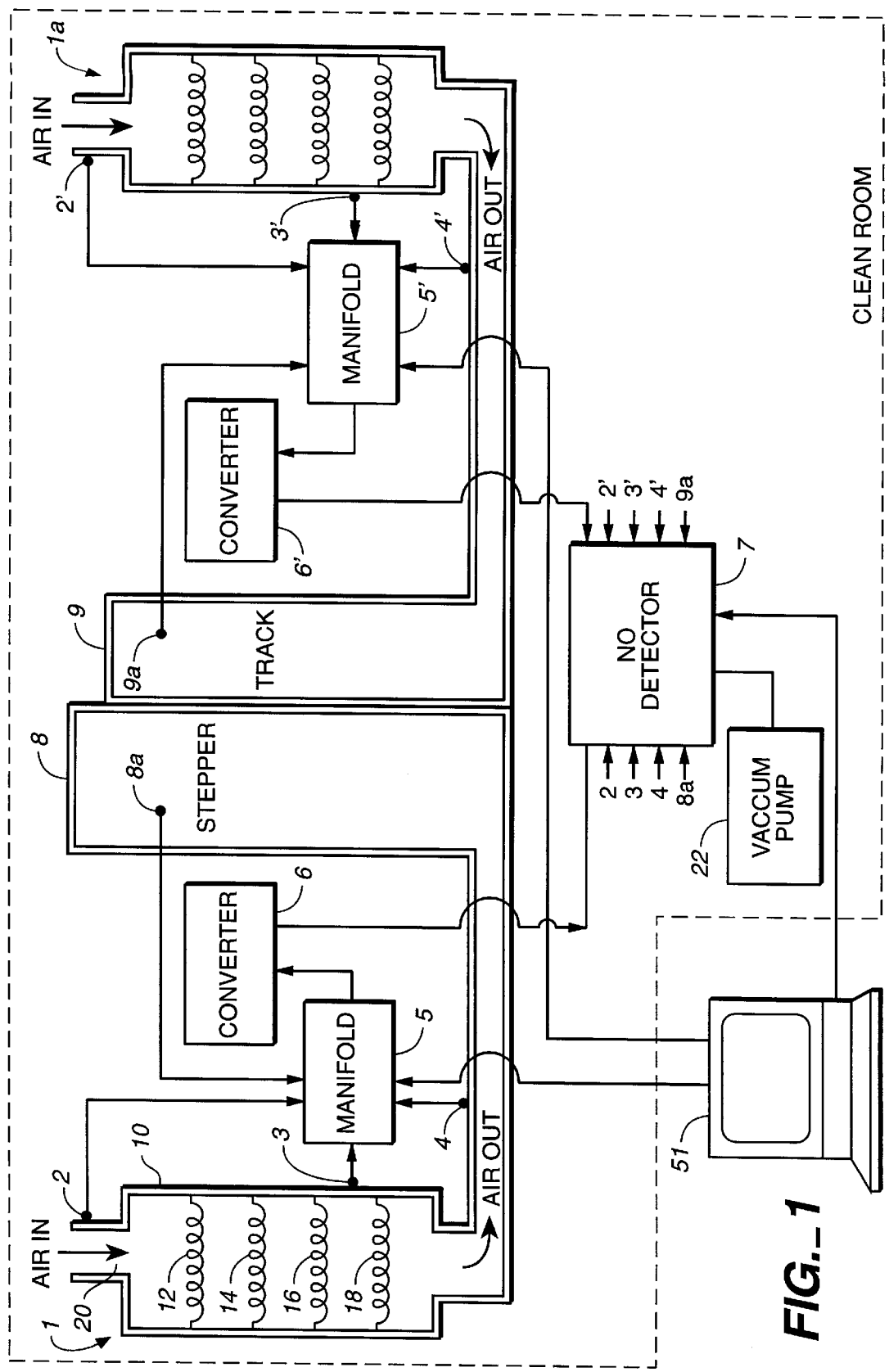
FIG._1

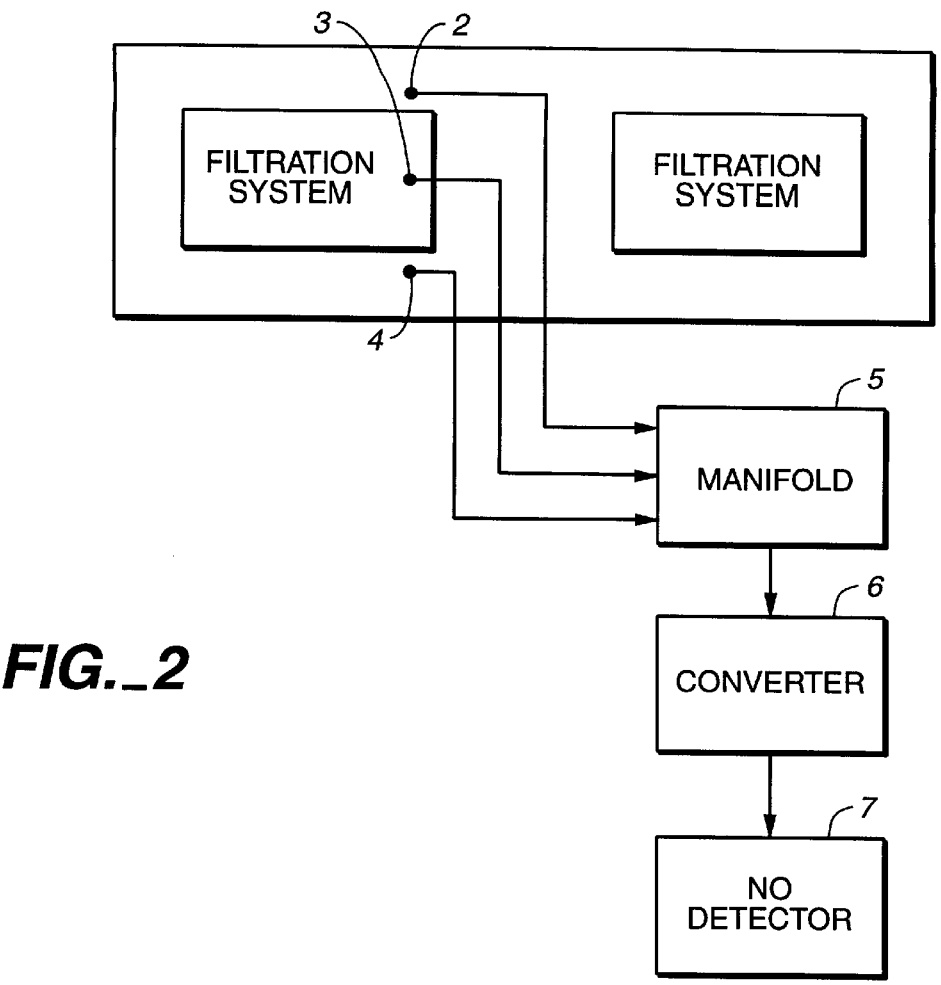
FIG._2
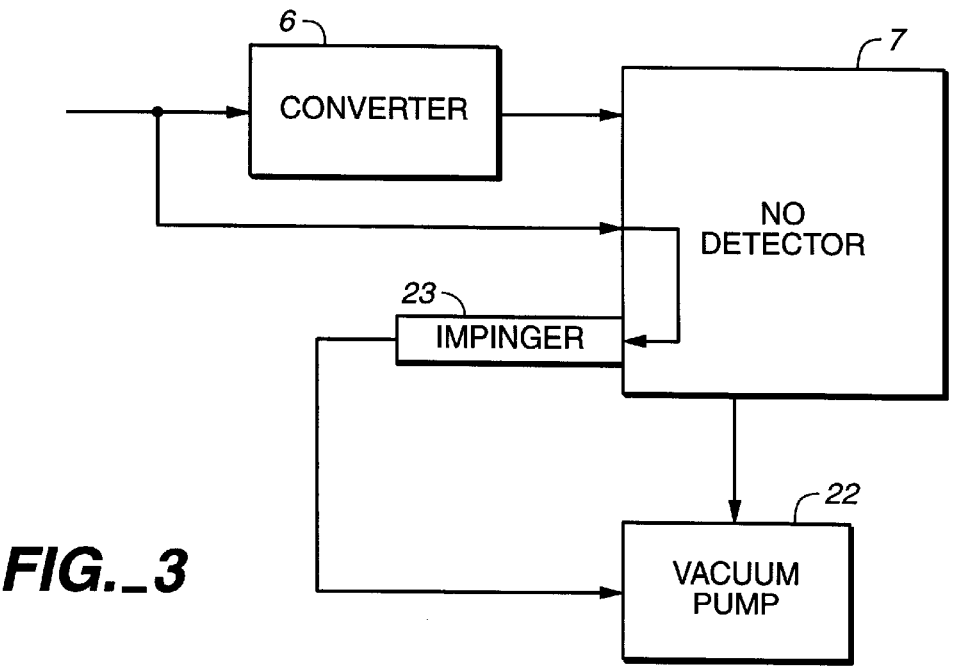
FIG._3

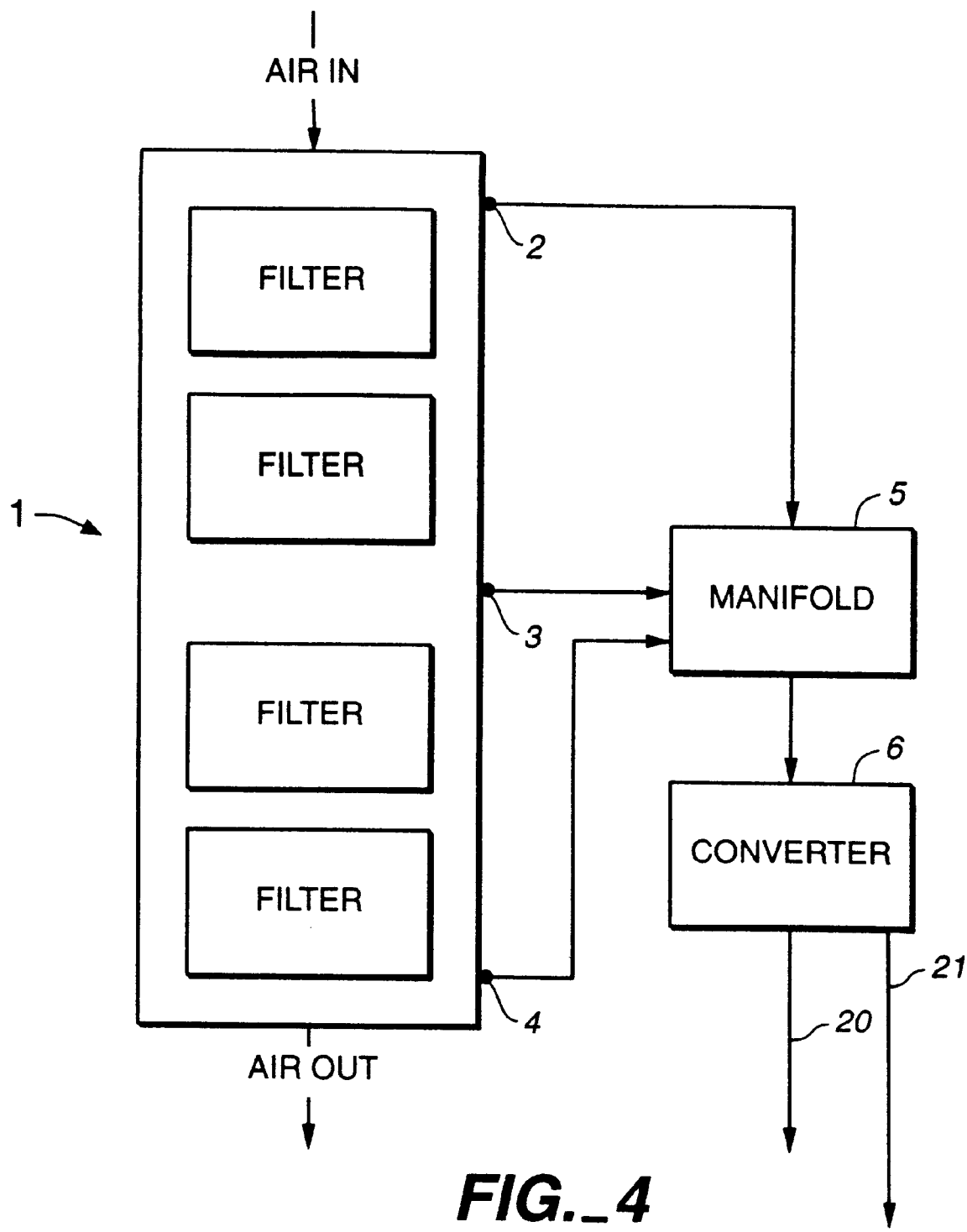
FIG._4

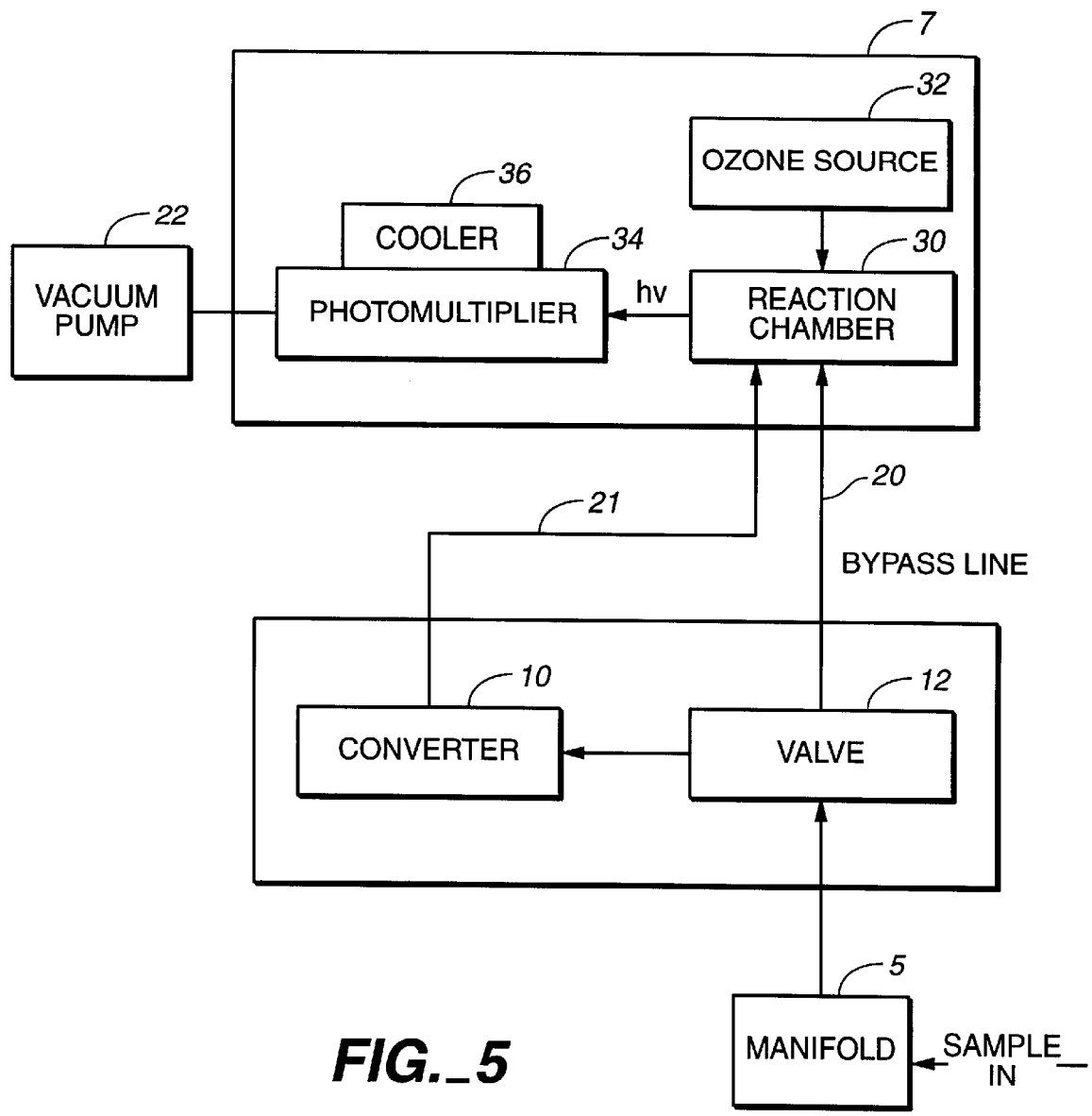
FIG._5

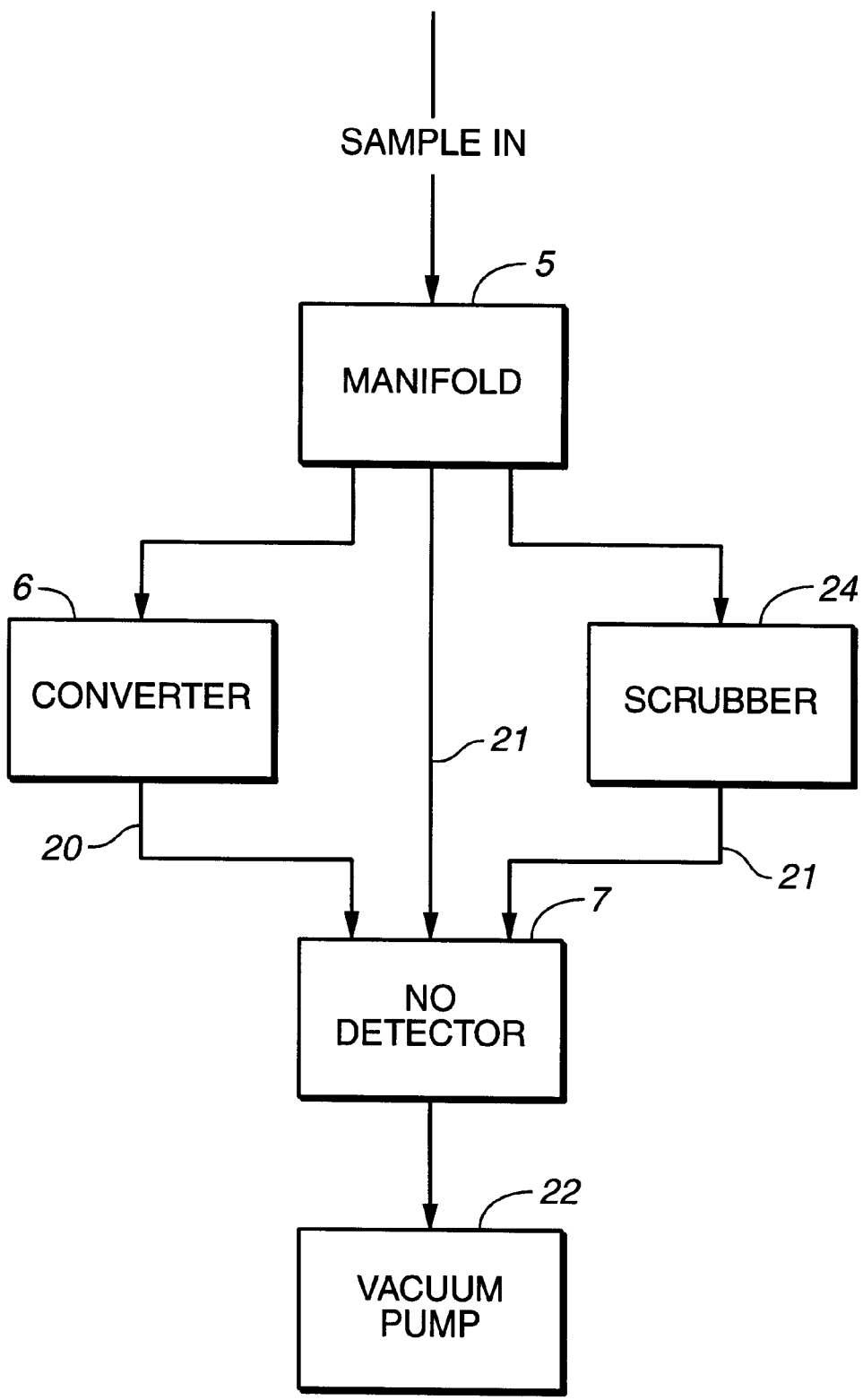
FIG._6

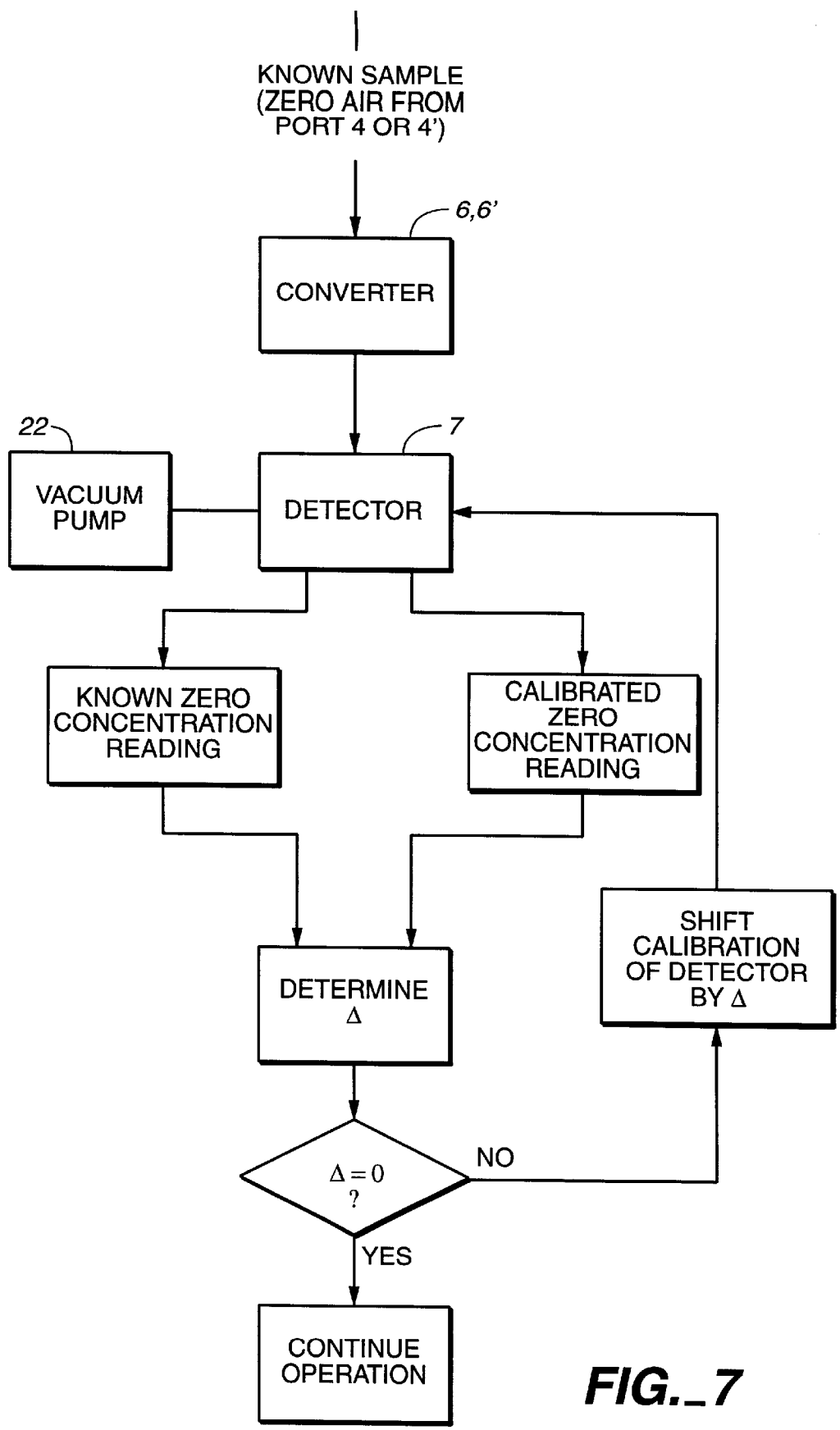
FIG._7

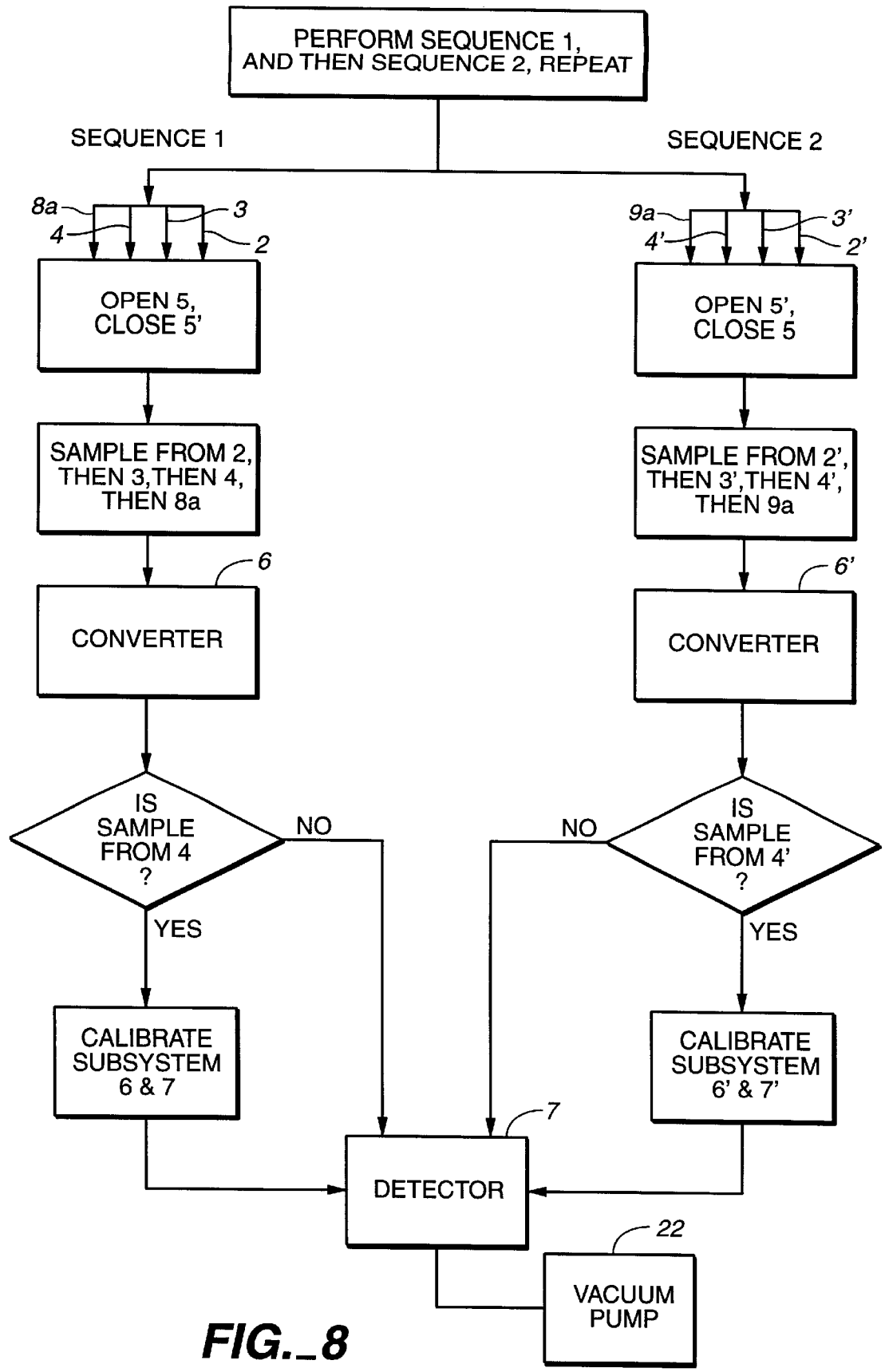
FIG._8

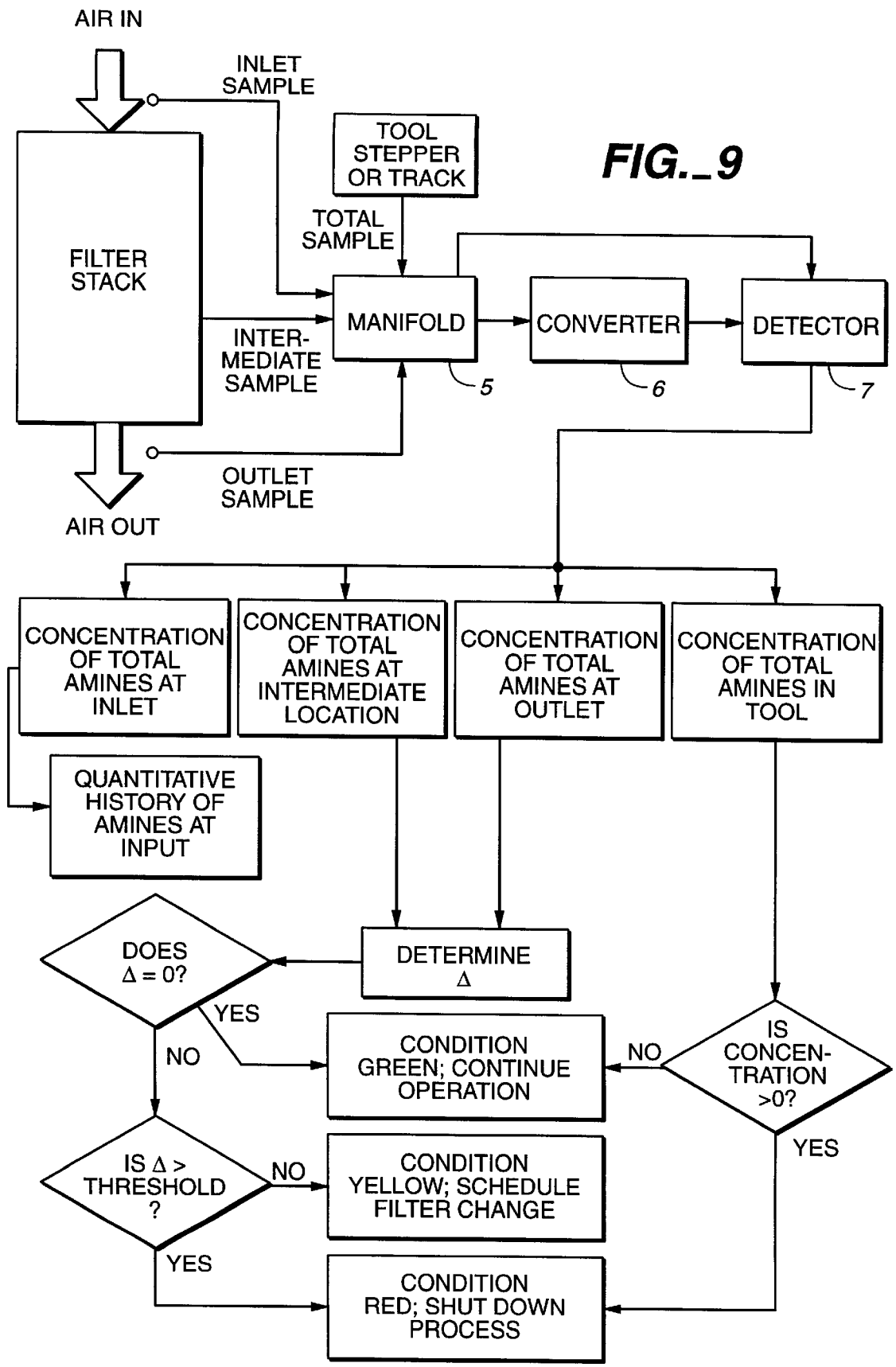
FIG._9

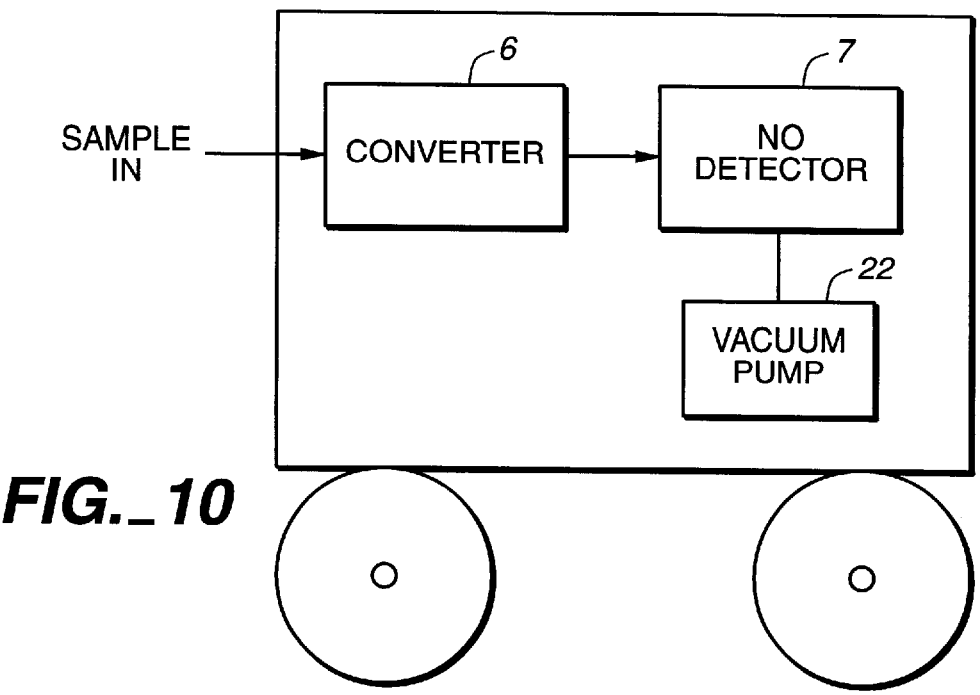
FIG._10
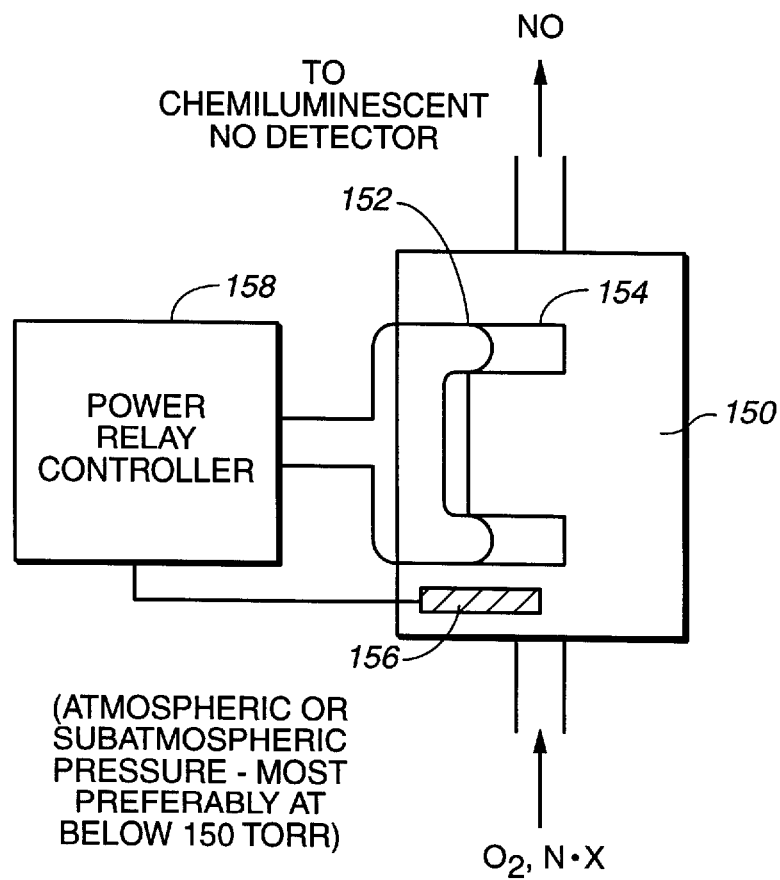
FIG._12C

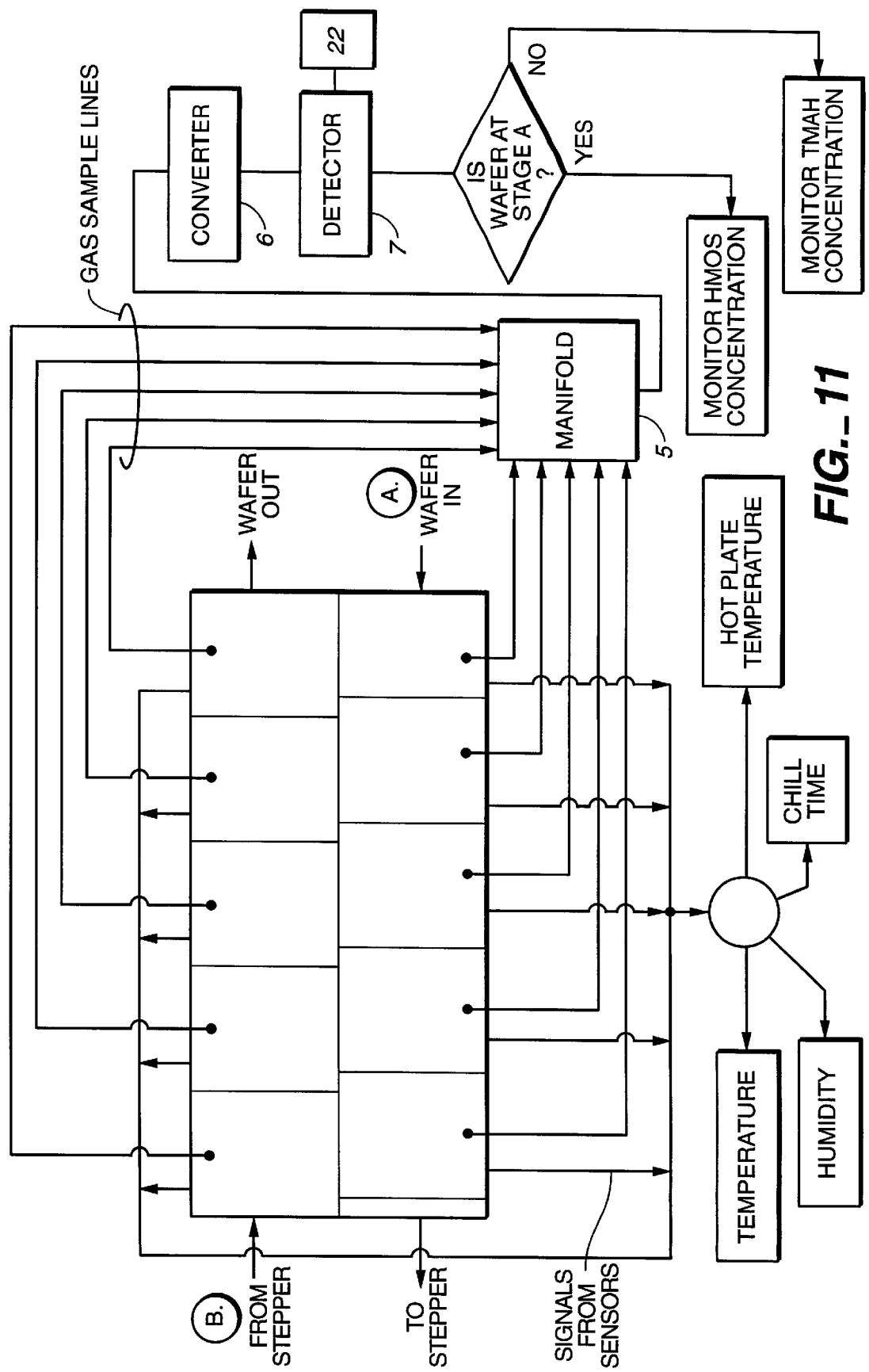
FIG._11

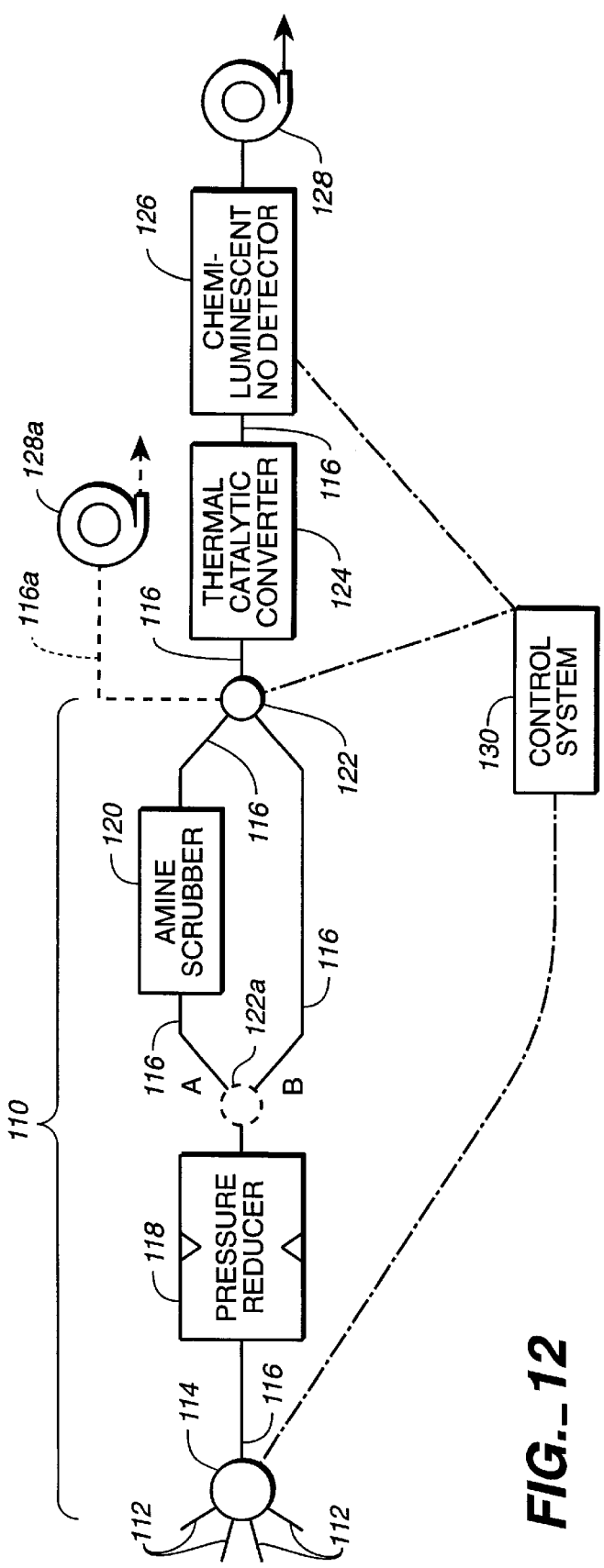
*FIG._12*
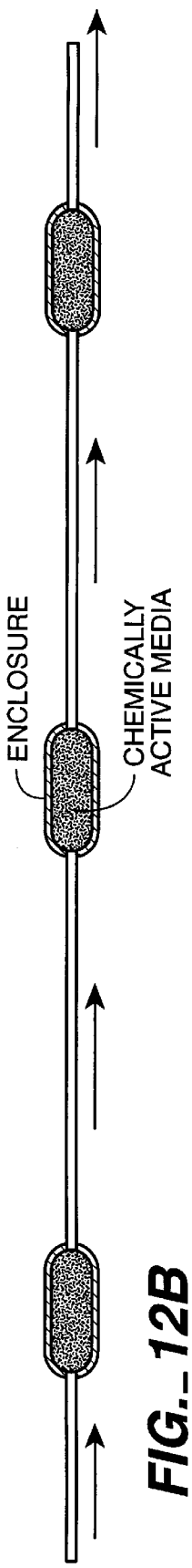
*FIG._12B*

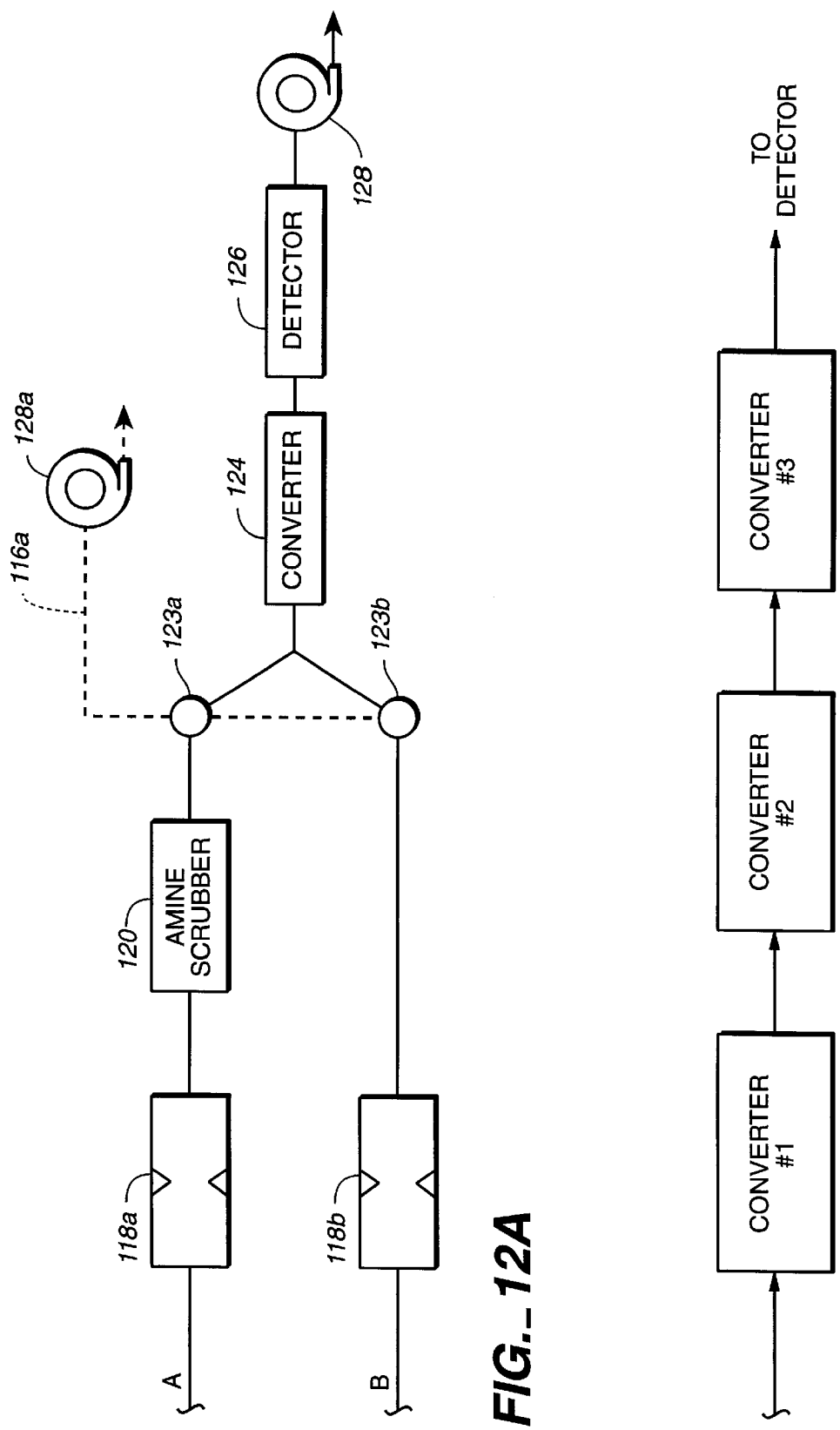

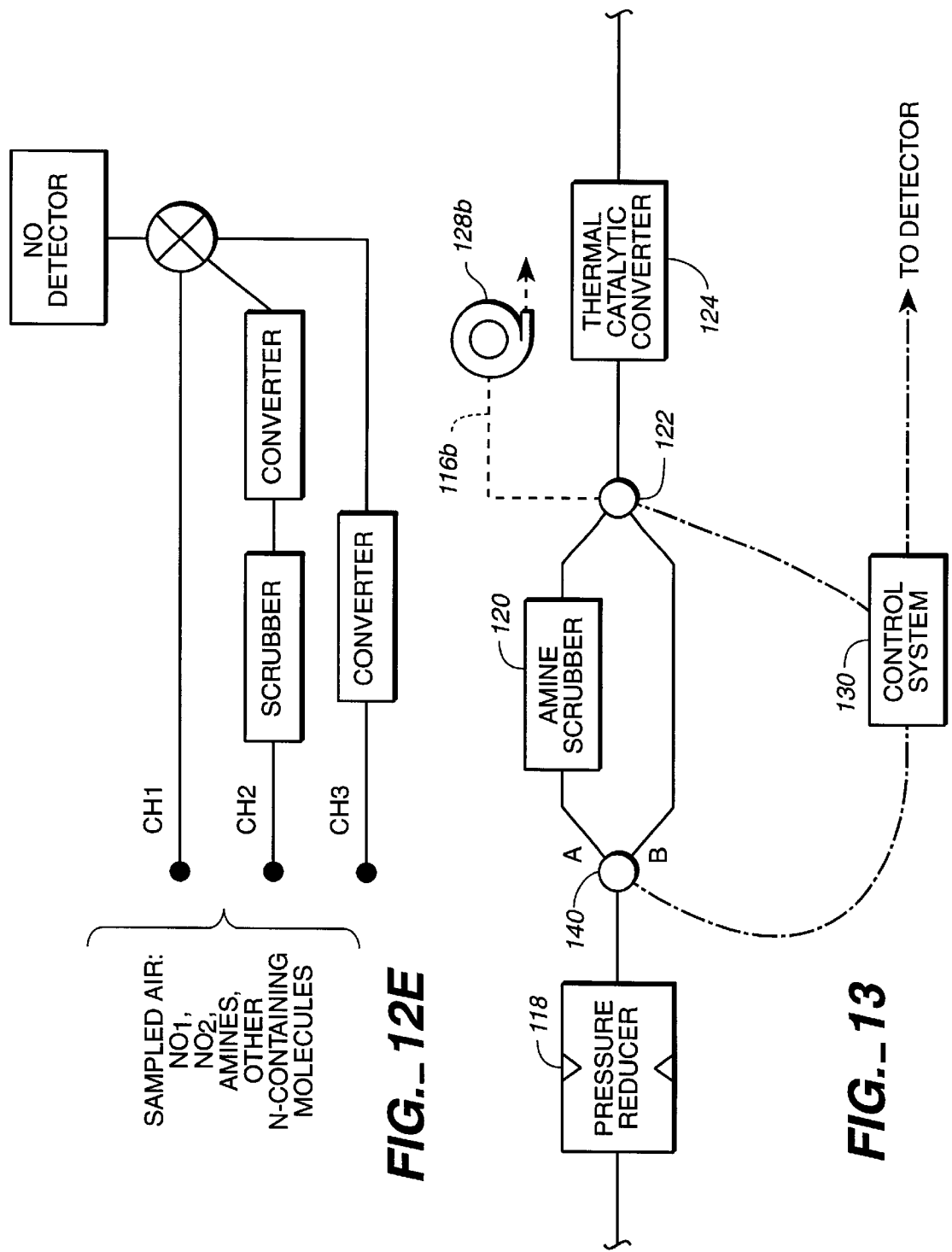

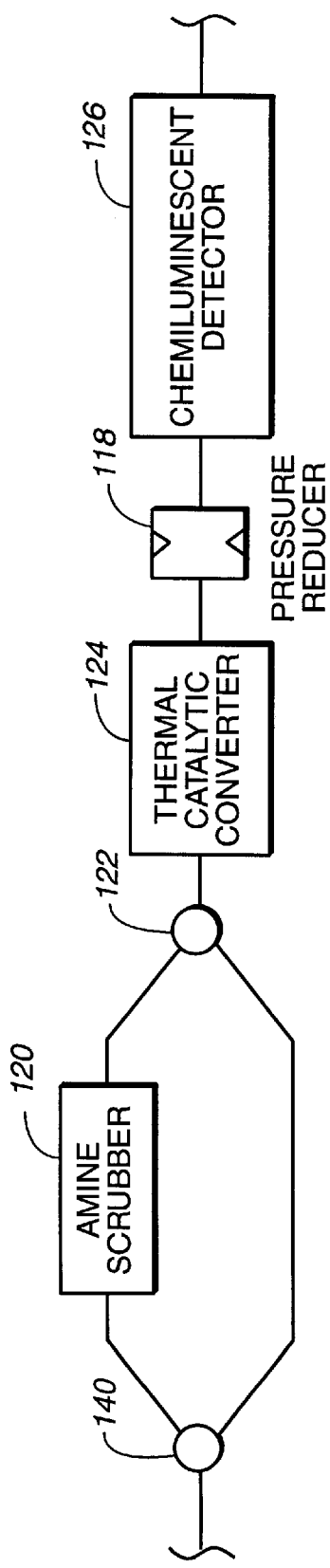
FIG._14
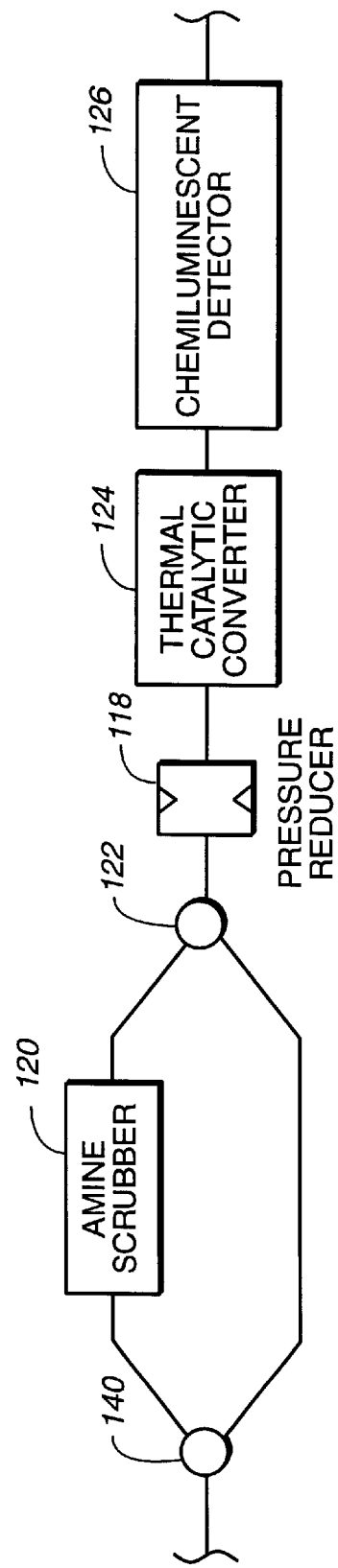
FIG._15

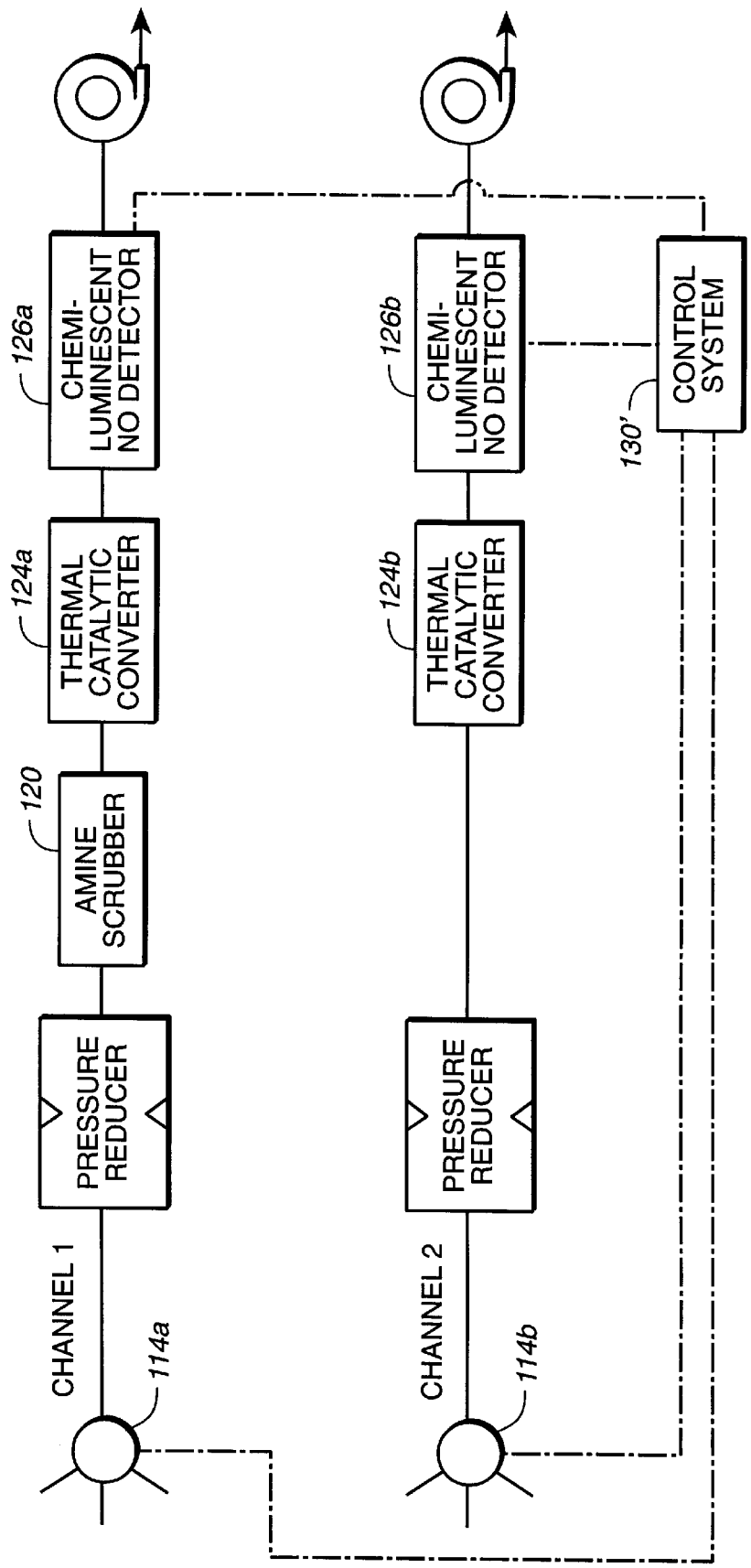
FIG._16

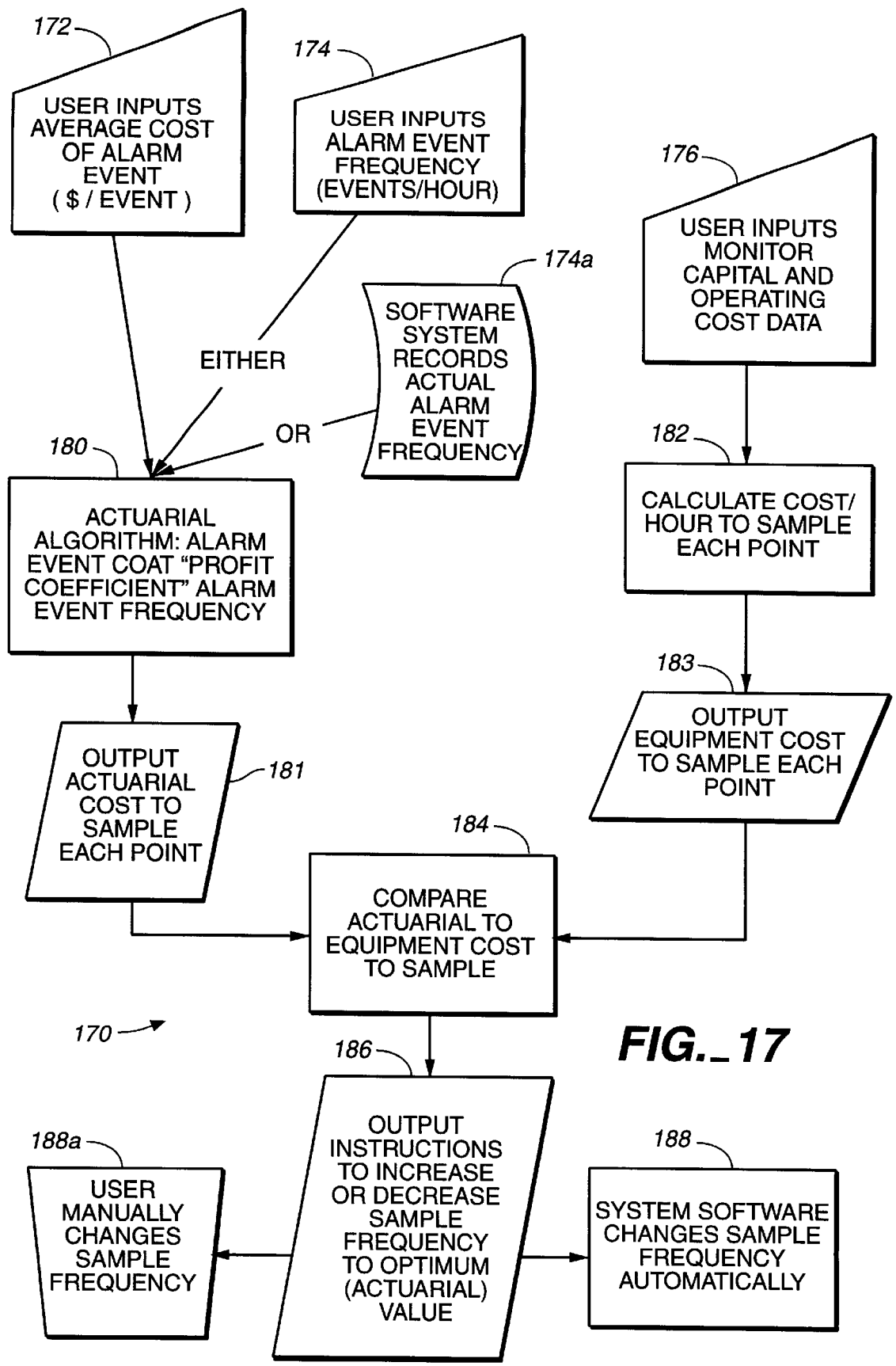
FIG._17

| CHANNEL | | ALARM EVENT FREQUENCY | COST OF ALARM EVENT | NOT OPTIMIZED SAMPLE FREQUENCY | EQUIPMENT COST | ACTUARIAL | SAMPLE FREQUENCY | OPTIMUM SAMPLE |
|---|---|---|---|---|---|---|---|---|
| CHAN-NEL | DESCRIP-TION | (EVENTS/ HOUR) | ($/AVG. ALARM EVENT) | (SAMPLES/ HOUR) | COST/HOUR TO SAMPLE | COST/HOUR TO SAMPLE | INSTRUC-TIONS | FREQUENCY (SAMPLES/ HOUR) |
| 1 | STEPPER STAGE | 6.00E-03 | $7,000 | 0.86 | $16 | $84.00 | INCREASE FREQUENCY TO | 4.43 |
| 5 | STEPPER INTER-STACK | 2.00E-04 | $7,000 | 0.86 | $16 | $2.80 | REDUCE FREQUENCY | 0.15 |
| 6 | TRACK INTER-STACK | 2.00E-04 | $7,000 | 0.86 | $16 | $2.80 | REDUCE FREQUENCY | 0.15 |
| 2 | INTER-FACE | 6.00E-03 | $7,000 | 0.86 | $16 | $84.00 | INCREASE FREQUENCY TO | 4.43 |
| 3 | TRACK, PRE-EXPOSE | 6.00E-03 | $7,000 | 0.86 | $16 | $84.00 | INCREASE FREQUENCY TO | 4.43 |
| 4 | TRACK, POST EXPOSE | 6.00E-03 | $7,000 | 0.86 | $16 | $84.00 | INCREASE FREQUENCY TO | 4.43 |
| 7 | PHOTO BAY | 1.40E-03 | $2,000 | 0.86 | $16 | $5.60 | REDUCE FREQUENCY | 0.30 |

FIG._18

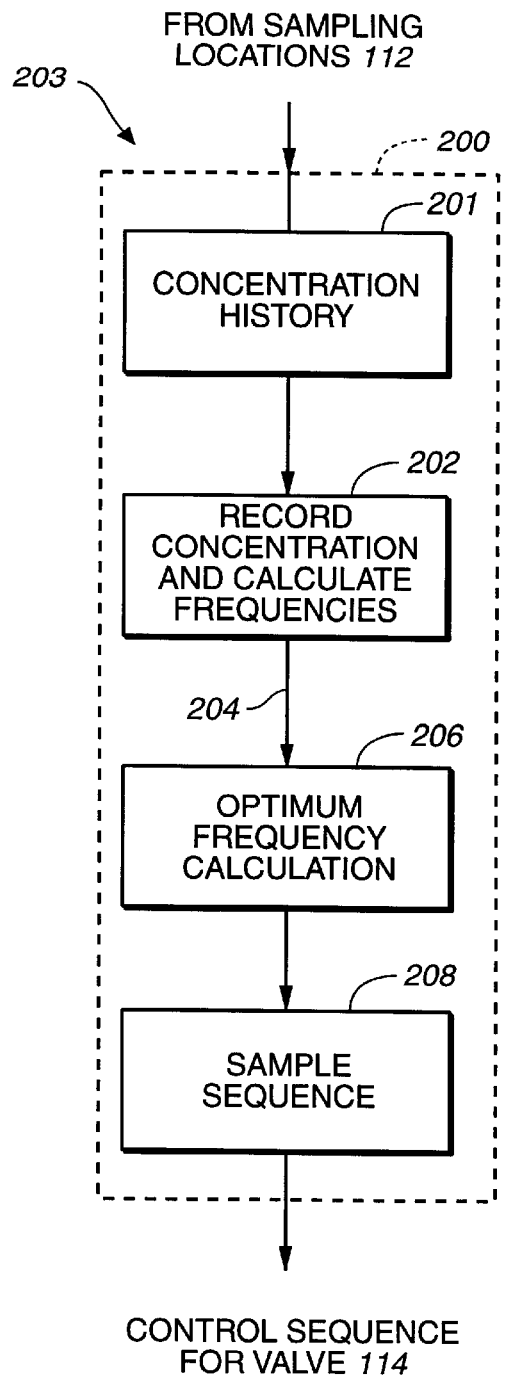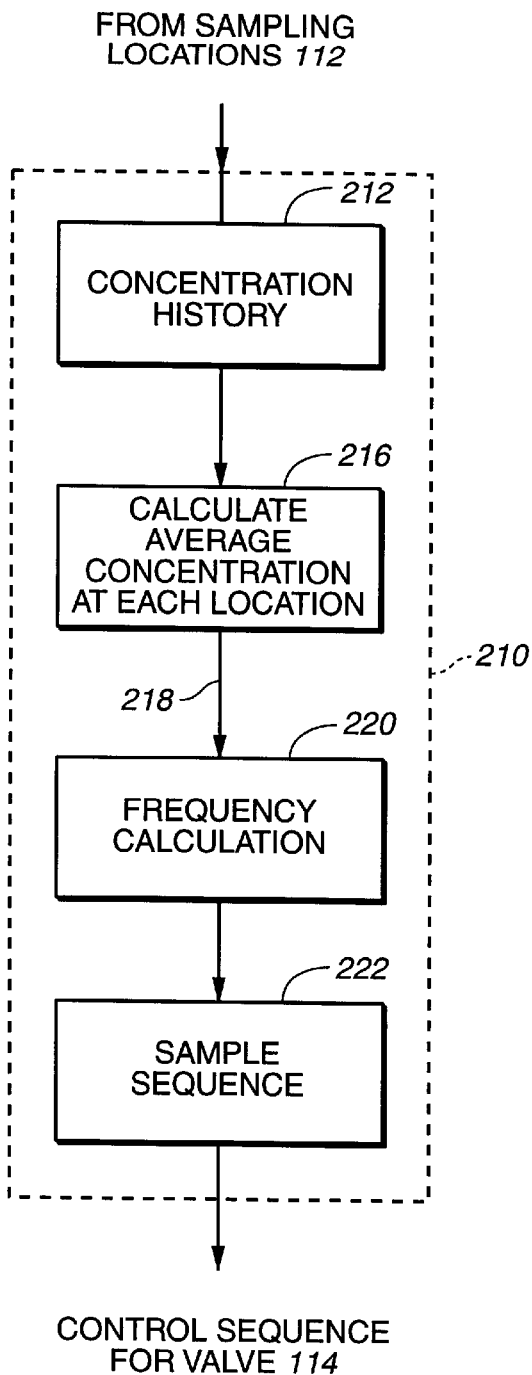
FIG._19      FIG._20

PROTECTION OF SEMICONDUCTOR FABRICATION AND SIMILAR SENSITIVE PROCESSES

This is a continuation-in-part of U.S. application Ser. No. 08/795,949, filed Feb. 28, 1997, now U.S. Pat. No. 6,096,267.

BACKGROUND OF THE INVENTION

The invention relates to the detection of base contaminants in air, especially amine contaminants, and to systems employing such detection, including semiconductor fabrication systems and systems for filtering air for semiconductor fabrication and other processes that require uncontaminated air of high quality.

A particular purpose of the invention is to reliably measure low concentrations of airborne base contaminants in a semiconductor manufacturing environment that may adversely affect base-sensitive photolithographic processes being employed.

In semiconductor manufacturing it has been found desirable to detect an organic amine such as NMP (normal methyl pyrrolidinone) or ammonia. Such a contaminant may interfere for instance with a photolithography process used in semiconductor fabrication. The base contaminant may react with protons produced as a result of exposure of a photoresist layer to light. This can interfere with proper exposure and can harm the yield of the process and the rate of production of the semiconductor wafers.

For this reason, semiconductor manufacturers have sought to measure and control the concentration of airborne molecular contamination during the critical steps of the photolithography process which are sensitive to it. A detecting instrument specific to the detection of NMP and a detecting instrument specific to the detection of ammonia have been employed in semiconductor manufacturing facilities to monitor the air quality in the vicinity of production tools.

To understand the novel aspects of the invention it is useful to mention some detection techniques that have been used in other contexts.

For study of combustion processes or atmospheric pollution, U.S. Pat. Nos. 4,333,735 and 3,647,387 disclose processes for measuring the total fixed gaseous nitrogen species, including $NH_3$, NO, $NO_2$, HCN and organic amines in gaseous mixtures. The process involves catalytic conversion at elevated temperature of all fixed nitrogen species to NO, followed by chemiluminescent measurement of the resulting NO concentration.

For detection of ammonia, NO and $NO_x$, U.S. Pat. No. 3,904,371 and products from various instrument manufacturers, including Thermo-Environmental, Advance Pollution Instruments, and Instrumatics International, employ an ammonia scrubber or absorber coupled with a thermal/catalytic converter with or without a molybdenum catalyst. For instance, in the Instrumatics instrument for stack gas analysis, a diluted sample is directed by a valve to alternatively flow through or past an absorber that specifically removes ammonia. The alternating samples proceed along a common line through a thermal converter to a chemiluminescent detector that operates in the 650–750 millibar range. By subtracting signals, the ammonia concentration can be calculated.

U.S. Pat. No. 5,057,436 discloses the use of an ammonia scrubber, positioned between two ammonia detectors, to measure the ammonia level in air.

Another aspect of the invention relates to the use of air filters for the ambient air in semiconductor manufacturing. To avoid harm to the process from NMP or ammonia, semiconductor manufacturers have used chemical filters to remove the contaminants. These filtering systems employ filter stages within an enclosure, the filter media of each stage being penetrable by air with acceptable pressure drop. As air flows through the filtering system, unwanted contaminants are retained on the chemically active surface of the various stages of the filter system. A problem associated with such filtering systems has been to accurately predict the remaining life of the filter so that the filter media can be changed at appropriate times with minimal disruption to the use of the expensive production facility. In the case of semiconductor fabrication facilities, typically, filter life has been estimated by measuring the concentration of ammonia in the air flow associated with the filter system.

SUMMARY OF THE INVENTION

The measurement of ammonia only is not satisfactory to photolithographic processes that are affected by low concentration of any basic material or amines, such as chemically amplified DUV photoresist processing. The measurement of total fixed nitrogen species is not applicable because many of the species (e.g., HCN, NO, $NO_2$) are not basic in nature and do not affect the process. Detection of ammonia at high concentrations is not useful for the monitoring of amines at low levels.

None of the techniques mentioned above have suggested the concept of the present invention of measuring in a single, non-specific reading, the concentration at low levels of the multiple amines in air exposed to photolithographic processes and the like, that will be described more fully below.

The invention is based at least in part on the realization that semiconductor manufacturing and in certain other processes, which are recognized to be sensitive to NMP, ammonia, or other amines, are in fact sensitive to the total proton-bonding capability of all base contaminants present, regardless of the specific identity of the amine contamination. According to the invention, rather than determine the presence and concentration of each individual contaminant by a separate detector, it is realized that important advantages can be obtained by providing a detector that provides a single reading that is stoichiometrically related to the aggregate proton-bonding characteristic of various base contaminants that may be present in the monitored air. In this way a "total amine detector" is provided.

As explained further below, what is recognized to be of use is a measurement of the totality of those multiple amine contaminants in the air that can adversely affect the process being monitored. For instance, currently-employed deep UV photolithography processes are sensitive to both strong and weak bases, hence, according to the present invention, all airborne amines are measured down to low concentration levels. In other cases, where the process is sensitive only to bases greater than a certain pH, then the system is implemented, according to this idea of the invention, to measure the totality of the multiple amines within the pH range to which the process is sensitive down to low concentration levels.

In important implementations of the invention, a system and method are provided that employ a converter to convert ammonia and other low or medium molecular weight amines, to a single detectable gas, which is then detected. Preferably, the contaminants are converted to NO (nitric oxide) molecules and the NO is detected with an $NO_x$ detector by subtracting from the total $NO_x$ reading, the $NO_x$ originally present in the sample as it was introduced into the converter. In a preferred implementation, the conversion is produced by thermal oxygenation. In various specific implementations, a heated stainless steel surface, a heated quartz surface or a catalytic conversion surface is employed to accomplish the oxygenation.

According to other aspects of the invention, advantages are obtained by placing the converter near the sampling site. In various implementations, the sampling site is a stage of a process affected by the contaminant, such as the stepper or track stage of a photolithographic tool cluster, or a part of the air filtration system, or the incoming air, or a region where contamination could arise such as a chemical storage locker. In these cases, sampling lines for unconverted and converted samples extend from the local converter to a remote NO detector. In certain cases, it is also advantageous that a number of such converters are employed to provide sampling capabilities in different locations, with each converter connected to the centralized detector.

One of the advantages of having the converter near the tool or other sampling site concerns the ability to obtain rapid stabilization of the detection cycle and, correspondingly rapid accurate readings, to give early warning of any contamination problem. Amine contaminants have a high adsorption coefficient relative to the interior surfaces of typical sampling lines, and deposits of amines in long sample lines can require long periods of flushing until a stable reading is obtained. On the other hand, the converted gas, NO, has a low adsorption coefficient relative to the sample line surfaces. Thus, by localizing the NO converter at the site to be monitored, only a short sample line is subject to adsorption of amines, while the extended line between the converter and the remote detector conducts air containing relatively non-adsorptive NO. In this manner, the sampling cycle can be of very short duration, to provide early warning for the detection of unwanted contaminants.

In semiconductor clean rooms, for instance those in which deep UV photolithography is conducted, a series of chemical filter stages is employed for the air supply. The flow of air passes successively through the filter stages to provide deep cleaning of the air to remove airborne amines.

According to another aspect of the invention, one or more conditions relevant to the operation of a total amine detection system is determined from the filter system, and in another aspect of the invention one or more conditions relevant to the operation of the filter system is monitored by the total amine detector system.

In a preferred implementation, a sampling port is located downstream of the filter system to monitor the filter output, and at least one additional sampling port is disposed between stages of the filter (at an intermediate location). In preferred arrangements, another sampling port is localized upstream of the filter system to monitor the chemical contamination to which the system is being exposed over time.

To enable calibration of the zero point of a total amine detection instrument, the downstream outlet port provides zero air (air free of amine contamination) for on-site calibration of the instrument. In certain instances, the calibration is performed manually by the operator, while in other implementations the calibration proceeds automatically on a periodic or continuous basis. The fidelity of the zero air from the downstream port is guaranteed as long as the concentration of contaminants at the intermediate sampling port is also zero.

During normal use of the filter system, the difference in the concentration of the contaminants measured between an intermediate port and the downstream outlet port is zero, as the preceding stage(s) of the filter are effective to remove all amine contaminants. The detection system is arranged to measure this differential for use for determining the validity of the zero reference. When the differential becomes greater than zero, or alternatively, when the differential reaches a certain value that still predicts that the output has ceased to contain zero amines, the differential reading is taken to determine the reliability of the zero output of the filter for calibration purposes.

A differential reading between the outlet and an intermediate sampling point is also advantageously employed to indicate the time when the elements of the filter system should be replaced. A zero differential reading indicates all of the contaminants are still being removed by the filter stages upstream of the intermediate sampling port, while a positive value indicates that some contaminants have reached the intermediate point and can only be removed in the final stage of the filter.

Another way of predicting the time for filter replacement employs the total amine detector to detect total amines from a sample port upstream of the filtering system. This provides information regarding the past history of contaminant concentration in the airflow that has passed through the filtering system. The contamination of air entering the system may change because of the season of the year, industrial or agricultural activity in the region, or accidental spills within the facility. The overall contamination rate is monitored over time at the upstream sample port. And, by correlation of this history of contaminant loading with the past performance of the filter, as monitored at an intermediate stage, the amount of filter life remaining is projected, and the time is set when the filter elements should be changed.

In a system combining these features, information from the sampling port at the outlet of the filtering system is employed to assure that no contaminant enters the environment to be protected, the intermediate port is employed to provide for early warning, and the upstream sample is employed to provide information about background contamination and is used to determine filter performance.

In certain instances, multiple intermediate sampling ports are employed along the filtering system, to provide further information to assist in indicating when change of the filter elements should be scheduled. The intermediate port closest to the outlet can be employed to verify the fidelity of the outlet air as a zero reference for the detection system.

According to a further aspect of the invention, the same converter is used in conjunction with monitoring the performance of an air filtering system and monitoring the environment of a particular tool, or process with which the air filtering system is associated. In this arrangement, zero air calibration can be provided simultaneously for the reading for both the tool or process and the filter system. In important examples where a centralized detector serves multiple converters that monitor different regions, each subsystem of a converter and the detector is advantageously treated as a separate calibration entity that is separately calibrated using, for zero reference, a sampling port at the outlet of the filter system that serves the respective sampling region.

In one aspect, the invention features, a detection system for detecting base contamination at low concentrations in gas characterized in that the detection system is constructed to examine multiple amines in gas to produce a reading stoichiometrically related to the proton bonding characteristic of the multiple amines present. The detection system comprises at least two channels through which a gas sample to be examined passes, at least one convertor for converting the multiple amines into NO, and at least one chemiluminescent NO detector for producing signals representative of the NO concentration in air passing therethrough. The total amine concentration is determined from the difference between the detected NO concentrations passing through the channels.

In another aspect of the invention, the detection system comprises a convertor for converting the multiple amines into NO.

Embodiments may include one or more of the following features.

The chemiluminescent NO detector may be operated at 125 millibar, suitable for detection of low amine concentrations. A pressure reducer may be located upstream of the detector and a vacuum may be located downstream of the detector. The pressure reducer may comprise a calibrated glass capillary heated to reduce the amine-sticking coefficient. The detection system may be constructed to effect thermal conversion of amines into NO at a substantially reduced pressure relative to ambient. The pressure reducer may be located upstream of the converter, and the amines remover may be constructed to effect scrubbing at a substantially reduced pressure relative to ambient. The pressure reducer may be located upstream of the amines remover.

The amines remover may comprise an amine scrubber, which may contain a strong cation exchange resin. The channels may share a common convertor and a common detector, and a system for cyclically directing sample gas slugs from the channels through the common converter and the common detector may be provided. The amines remover may be incorporated into only one of the two channels. A multi-way valve may be arranged for selecting which of the channels air may flow through to the converter. A pump may be coupled to the multi-way valve for maintaining substantially steady state flow conditions through one or both of the channels. A second multi-way valve may be positioned upstream of the amines remover and upstream of the multi-way valve for isolating the amine remover. Separate pressure reducers may be provided in each of the channels; each of the pressure reducers being calibrated such that the pressure drop in the channel with the amine remover is equivalent to the pressure drop in the other channel.

A controller may be provided for alternately coupling each channel for fluid flow to the detector, wherein the controller is operable to alternately couple between channels at a frequency of less than 10 minutes. Separate instruments may be assigned respectively to the two channels, a first of the channels including an amines scrubber followed by a thermal/catalytic converter coupled to an NO detector, and a second of the channels comprising a thermal/catalytic converter coupled to NO detector, whereby the possibility of noise from intra-calculation cycle concentration variations of NO and NO2 can be avoided.

The amines remover may be constructed to remove only multiple amines of interest from air passing through one of the channels. The system may be combined with a photoresist system for conducting a process which is particularly sensitive to a limited class of multiple amines, wherein the amines remover is constructed to selectively remove the limited class of amines to which the process is particularly sensitive. The amine remover may comprise photoresist coated beads, the photoresist coating corresponding to the photoresist of the process. The detection system may be constructed and arranged to sense the emissions of construction materials used in implementing an amine-sensitive process. The detection system may be adapted to monitor the performance of an amine filter system used to filter a DUV stepper, scanner or coat/develop track. The detection system may be adapted to monitor the total amine concentration inside a DUV stepper, scanner, or coat/develop track. The detection system may be adapted to monitor cleanroom concentration of total amine concentration inside a DUV stepper, scanner, or coat/develop track. The detection system may be adapted to monitor the total amine concentration inside a chemical cabinet serving a DUV stepper, scanner, or coat/develop track.

The channels may comprise stainless steel tubing coated with silica. The silica may be deposited on the channel tubing using chemical vapor deposition. The channel tubing is heatable substantially along its total length to reduce amine deposition on the walls of the tubing. The channels may comprise glass tubing, which may be coated with silica. The glass tubing is heatable substantially along its total length to reduce amine deposition on the walls of the tubing. The glass tubing may be reinforced with epoxy.

A control system may be provided for monitoring and controlling the system. The control system may be operable to implement a process for lowering the amplitude of intra calculation cycle concentration variations of NO and $NO_2$. The process may be based on a moving average. The moving average may be selected to smooth the noise in the measurement in a manner that diminishes over-time as the number of averaging cycles increases. The control system may be operable to implement an actuarial process that controls the sampling frequency of multiple sample locations in a monitoring system based on sample cost, such that the points of greatest sensitivity and importance are monitored with greatest frequency. The control system may be operable to implement a series of processes for determining the location of an amine leak by providing an automatic direction finder based upon increasing pollutant concentrations. Part of the detection system may be mobile and can be manipulated by the processes to determine the location of an amine leak. The control system may be operable to implement a series of processes for controlling a multi-channel base contaminant monitor by determining a sampling strategy for the channels based on the frequency with which the channels exceed a predetermined level. The control system may be operable to implement a series of processes for controlling a multi-channel base contaminant monitor by determining a sampling strategy for new channels based on the frequency with which existing channels exceed a predetermined level. The control system may be operable to implement a series of processes for controlling a multi-channel base contaminant monitor which calculates the sequence of channel monitoring based upon the similarity of the average concentration of contaminants measured.

At least one additional amines remover may be coupled in series with the first amines remover. At least one additional converter may also be provided. One or multiple amine removers and converters may be located proximal to a sampling point and are coupled to one or more NO detectors located remotely, whereby chemically stable molecule NO may be transferred to the one or more remote detectors.

In yet another aspect, the invention features an amines detection system comprising: a first air channel for delivering a reference air sample; a second air channel for delivering a target air sample; a converter coupled to the second air channel for converting molecular amine contamination in the target air sample into NO; a chemiluminescent NO detection system coupled to the first and second air channels for determining the NO concentrations in the reference air sample and in the target air sample; and a pressure reducing system coupled to the chemiluminescent NO detector for reducing operating pressure of the chemiluminescent NO detector to a level of 150 millibar or lower; whereby a total amine contaminant concentration in the sampled air may be determined from the difference between the determined NO concentrations in the target air sample and in the reference air sample.

The pressure reducing system may comprise a flow restrictor. The first and second air channels preferably have respective character flow diameters, and the pressure reducing system comprises a pressure reducer located upstream of the chemiluminescent NO detector and having an air channel with a characteristic flow diameter that is smaller than the characteristic flow diameters of the first and second air channels. A vacuum pump may be located downstream of the chemiluminescent NO detector. The pressure reducing system may be operable to reduce the operating pressure of the chemiluminescent NO detector to a sub-atmospheric level sufficient to achieve an NO detection sensitivity of 1 ppb or lower. A sampling port may be coupled to the first and second air channels; the sampling port providing the sampled air to the first and second air channels. An amines remover may be coupled to the first air channel for removing amines from air flowing in the first air channel to thereby produce the reference air sample.

In another aspect, the invention features an amines detection system comprising: a first air channel for delivering a reference air sample; a second air channel for delivering a target air sample; the first and second air channels being defined by respective elongated tubes having interior surfaces, which are substantially inert to amines, exposed for contact with air flowing therethrough; a heating system for heating the first and second air channels; a converter coupled to the second air channel for converting molecular amine contamination in the target air sample into NO; and a chemiluminescent NO detection system coupled to the first and second air channels for determining the NO concentrations in the reference air sample and in the target air sample; whereby a total amine contaminant concentration in the sampled air may be determined from the difference between the determined NO concentrations in the target air sample and in the reference air sample.

The tubes defining the first and second air channels each preferably comprises an interior silica surface exposed for contact with air flowing therethrough. The first and second air channels are each preferably formed from glass tubes. The glass tubes may be reinforced with epoxy. The tubes defining the first and second air channels each may alternatively comprise a rigid outer layer and a silica inner layer.

In another aspect, the invention features a method of monitoring molecular amine contamination in sampled air, comprising: providing a reference air sample; providing a target air sample; converting amines in the target air sample into NO; determining by chemiluminescence, under pressure conditions of 150 millibar or lower, the NO concentrations in the reference air sample and in the target air sample; determining a total amine contamination concentration from the difference between the determined NO concentrations in the target air sample and in the reference air sample.

The NO concentrations in the reference air sample and in the target air sample may be determined by chemiluminescence at a pressure of 125 millibar or less.

In another aspect, the invention features a method of monitoring molecular amine contamination in sampled air, comprising: sampling air from a region; delivering sampled air to a scrubber for removing amines therefrom to provide a reference air sample; delivering sampled air to a converter for converting amines therein in NO to provide a target air sample; determining by chemiluminescence the NO concentrations in the reference air sample and in the target air sample; determining a total amine concentration from the difference between the determined NO concentrations in the target air sample and in the reference air sample.

The NO concentrations in the reference air sample and in the target air sample may be both determined within the same ten-minute period of time. The NO concentrations in the reference air sample and in the target air sample may be determined at substantially the same time.

We will now summarize important aspects of the invention. According to one aspect of the invention a detection system is provided for detecting base contamination at low concentrations in a gas, for instance to protect a sensitive process, characterized in that the detection system is adapted to examine multiple amines in the gas and to produce a reading stoichiometrically related to the aggregate proton-bonding characteristic of the multiple amines present.

Preferred implementations of this aspect have one or more of the following features.

The detection system is adapted to examine all air-borne amines. The detection system includes a converter arranged to convert multiple amine contaminants in a gas to a common detectable compound, and a detector is adapted to detect that compound. The converter of the detection system is preferably adapted to form said compound by thermal conversion. Preferably the converter is adapted to oxygenate the multiple amines to NO. Preferably, the detector for a common compound to which the various amines are converted is a chemiluminescent detector, preferably the converter converts amines to NO and the detector includes a reactor to react NO with ozone to produce photons for chemiluminescent detection.

In another preferred implementation, the detector is a calorimetric detector. In the preferred implementation, the detector is controlled to detect $NO_x$ from the sample line and $NO_x$ from the converter, and is constructed to subtract $NO_x$ of the sample from the $NO_x$ reading for the converted sample to determine the total proton-bonding characteristic of the concentration of the multiple amines within the air sampled. In certain preferred implementations the detection system includes an extended gas conduit disposed between a converter located in the vicinity of a sample region and a remote detector and the common gas, preferably NO, to which the converter is adapted to convert the amines, has a relatively low adsorption coefficient relative to the interior surface of the conduit.

Preferred implementations of the detection system include a calibration system which includes a permanent connection to a source of zero air, preferably the source of zero air being the output of a chemical filter system. Preferably the chemical filter system is arranged to filter air to be exposed to a chemical process which the detection system is arranged to monitor, preferably at least one sample line of the detection system being connected to detect amine contamination of air in the filter system preceding the outlet.

In certain preferred implementations, the chemical filter system comprises a series of filter stages through which air passes, and the contaminant concentration at a location preceding the outlet is measured relative to the concentration of the contaminant at the outlet to determine when air at the outlet is valid as a zero reference, preferably the stage preceding the outlet is located immediately preceding the last filter stage of the filter system.

In another implementation, the source of zero air is a dedicated zero-air generator, the zero-air generator comprising a filter for filtering the ambient air, or a liquid scrubber solution that filters the ambient air by bubbling the air through the solution.

In certain preferred implementations, the detection system of the invention is connected to an amine air filter system to monitor remaining filter capacity, preferably the filter system being connected to monitor the output of the filter system, and to monitor air preceding the outlet of the filter system. In preferred embodiments of such a system a differential detector for measuring the difference in readings between the outlet of the filter system and an intermediate point in the filter system is employed. Preferably the detection system is connected to monitor air entering the filter system, and the detection system is connected to monitor air samples from the inlet, the outlet, and at least one intermediate position of the filter system.

In certain preferred implementations, the detector receives sample from an air filter system that supplies air to the environment of an industrial process and receives sample from a region associated with the process.

In other implementations that convert the amines to a common detectable compound, the detection system includes a plurality of converters, a single detector and valving for alternatively connecting respective converters to the detector. Preferably for each converter, two conduits extend to the detector, one comprising a sample conduit sampling the gas prior to entry to the respective converter, and the other a converted sample conduit conveying the common detectable compound from the converter to the detector. Preferably the detector is connected to a vacuum pump employed to provide air flows of converted and unconverted sample gases to the detector. Preferably the detection system with this vacuum pump includes an impinger comprising a tube containing liquid scrubbing solution, the impinger being connectable at one end to the pump to draw unconverted sample air through the liquid, to provide a grab sample of contaminants in the sample air.

In another implementation, the detection system includes an additional line to direct unconverted gas through a scrubber to the detector to remove amines from the gas, preferably the concentration of $NO_x$ detected in the scrubbed gas by the detector is compared with the concentration of $NO_x$ in the unconverted, unscrubbed sample gas to verify the fidelity of the $NO_x$ readings of the detector.

In other preferred implementations, the detection system includes a calibration system constructed to establish separate calibration values in respect of each subsystem comprising the detector and a respective converter. The detector system preferably includes a separate source of zero air for calibrating each respective subsystem and, for each subsystem, the output of a chemical air filter of a type selected to filter air being sampled by the respective converter is preferably employed as a zero air reference.

Preferably, at least one detection subsystem receives sample air from an air filter system that supplies air to the environment of an industrial process, and at least one detection subsystem receives sample air from a region associated with the process. Preferably different steps of the industrial process have respectively different chemical air filter systems, and different detection subsystems are connected to sample the different steps and associated air filters.

In certain preferred implementations, the detection system is combined with a photolithographic semiconductor production system. Preferably, the detection system monitors air at a stepper of the production system, air at a coat and develop track of the production system, air exposed to the semiconductor work processes, the remaining filter life of an air filter system supplying air to the production system, contaminant concentrations at a stepper and a coat and develop track of the production system, and the difference between total amine concentration at the outlet of an air filter system and at an intermediate sample position of the air filter system, preferably to signal the replacement of filter elements of the filter system when the difference is above a specified threshold.

In another implementation for a method of industrial process monitoring, the detection system is employed to monitor the presence of total amine contaminants in the air that can adversely affect the process, preferably a deep UV photolithography process.

In another preferred implementation, the detection system comprises a converter adapted to convert to NO multiple amines present in an air sample, a chemiluminescence detector constructed to react the NO resulting from the amines to produce a reaction product having an excited state, and a photodetector responsive to photons emitted from the reaction product to determine the proton-bonding characteristic of the multiple amines present, preferably to monitor air quality for an environment of a deep UW photolithography process, the system having a sensitivity for 1 ppb or better of amine contaminants.

Preferably the converter is located near a stage of the process, the detector is located at a remote location, and sample lines conducting unconverted sample and converted sample extend between the converter and detector.

Preferably the photodetector is a photomultiplier tube, and a cooler is arranged to cool the tube to achieve sensitivity of at least about 1 ppb.

In other preferred implementations, the detection system monitors the total amine concentration at selected stages of a multistage manufacturing process, preferably the detection system monitors the total amine concentration of a coat and develop track tool in a deep UV photolithography process, preferably the concentration of an adhesive promoter employed during the stage of laying the photoresist at the track, and the concentration of a chemical employed during the developing stage at the track.

In another implementation a single detector is connected to monitor both the concentration of an adhesive promoter employed during the stage of laying the photoresist at the coat and develop track and the concentration of a chemical employed during the developing stage at the track.

In certain other implementations, the detection system is constructed as a mobile unit for detecting leaks in a multistage manufacturing process, preferably to localize leaks in regions of high amine contamination in a deep UV photolithography process.

In other implementations, the detection system monitors the total base loading within a clean room of a fabrication facility and provides a single reading for the total base loading for purposes of certifying the clean room. And in another implementation, the detection system monitors filter performance of a filter in either the make-up or recirculation air supplying a cleanroom, preferably to monitor total amines both upstream and downstream of a filter system comprising either a lone filter stage or a series or parallel arrangement of filter stages in the make-up or recirculation air system of the cleanroom.

BRIEF DESCRIPTION OF THE DRAWINGS

FIG. 1 is a plan view of a deep UV photolithography processing facility employing a contaminant detection system.

FIG. 2 is a diagrammatic view of parallel trays of filter media.

FIG. 3 is a diagrammatic view of an impinger drawing unconverted sample gas.

FIG. 4 is an enlarged view of the filtration tower shown in FIG. 1.

FIG. 5 is a diagrammatic view of a converter-detector subsystem of the detection system of claim 1.

FIG. 6 is a diagrammatic view of the converter-detector subsystem of FIG. 5 adapted to include a scrubber.

FIG. 7 is a flow diagram illustrating the process of calibrating the detection system of FIG. 1.

FIG. 8 is a flow diagram illustrating the continuous operation and calibration of the embodiment of FIG. 1.

FIG. 9 is a flow diagram illustrating the monitoring and control of the processing tools and filtration system of the embodiment of FIG. 1.

FIG. 10 is a diagrammatic view of a total amine detector as a mobile detection unit.

FIG. 11 is a diagrammatic view of a photolithographic system in which a total amine detector is combined with a track.

FIG. 12 is a diagrammatic view of a sample delivery train for total amine detection that has an amine scrubber to produce an internal reference, and in which a pressure reducer is located upstream of the amine scrubber.

FIG. 12a illustrates separate pressure reducers, FIG. 12b illustrates a scrubber arrangement, and FIGS. 12b and 12c illustrate thermal converter arrangements useful in the system of FIG. 12 and generally. FIG. 12d is a diagrammatic view of three converters coupled together in series. FIG. 12e is a diagrammatic view of a detection system that includes three separate sample channels coupled to an NO detector.

FIG. 13 is a diagrammatic view of a sample delivery train similar to that of FIG. 12 in which an isolation valve is located upstream of an amine scrubber.

FIG. 14 is a diagrammatic view of a sample delivery train similar to FIG. 13 in which the pressure reducer is located downstream of a thermal catalytic converter.

FIG. 15 is a diagrammatic view of a sample delivery train similar to FIG. 13 in which the pressure reducer is located downstream of an amine scrubber and a selection valve.

FIG. 16 is a view similar to FIG. 12 of a system implemented to be immune to variations in $NO_x$ at the sampling site.

FIG. 17 is a flowchart of a process for determining the optimum sample cost and sample frequency.

FIG. 18 is a table illustrating the operation of the process of FIG. 17.

FIG. 19 is a flowchart of a process for determining the sample sequence based on past performance.

FIG. 20 is a flowchart of a process for determining the sample sequence based on average concentrations.

DESCRIPTION OF THE PREFERRED EMBODIMENTS

In FIG. 1 a photolithography tool cluster is shown for the production of semiconductor wafers. The cluster consists of two tools, a stepper 8, and a track 9. Each of these tools is supplied by a separate clean air filtration system, 1 and 1a, respectively. The filtration tower comprises a metal enclosure 10 and a set of spaced apart chemically active filter stages 12, 14, 16, 18 installed in series within the enclosure.

As depicted in FIG. 1, the air enters at 20, at the top of the tower, the air being supplied from either outside the fabrication facility or from within the facility, or from within the clean room or the tool itself.

The filters are composed of chemically active composite materials, typically nonwoven fabric media to which are bound activated carbon particles that have been treated to remove ammonia and organic amines. The filter media is typically arranged as a set of pleats in the enclosure. An example of such filter media is known by the trademark Vaporsorb™, produced by the Assignee, Extraction Systems Inc. of Franklin, Mass., U.S.A.

In another embodiment, a converter-detector is employed to monitor filter performance of a filter deployed in either the make-up or recirculation air supplying a cleanroom. In this case, the converter-detector is employed in such a manner as to monitor total amines both upstream and downstream of a filter deployed either alone, or in-series in the make-up or recirculation air system of the cleanroom.

In other implementations, different filter media are employed. Certain examples include: parallel trays of loose activated carbon particles produced by e.g. Donaldson Company; extruded carbon blocks using a dry thermoplastic adhesive as the binding agent as produced by e.g. Flanders Filters, KX Industries, Peneer Industries; thin extruded carbon blocks manifest as a fabric as manufactured by e.g. KX Industries; media made by the modification of the chemical properties of the fiber structure as produced by e.g. Ebara Ltd. and Takuma Ltd.; and carbon fiber structures as produced by e.g. Kondo Limited; and carbon particle sheet media produced by e.g. Hoechst-Celanese.

As shown in FIG. 2, each filtration tower, 1 and 1a, includes, respectively, an upstream sampling port 2, 2', a downstream sampling port 4, 4', and an intermediate sampling port 3, 3'. Sampling ports 8a and 9a are likewise provided for the stepper 8 and track 9, respectively. For each filter and tool combination, there is one converter, 6 (for the stepper 8) and 6' (for the track 9). These two converters, 6 and 6', are connected to a common, remotely located $NO_x$ detector, 7. The detector, for instance, may be a Model 17 detector available from Thermo Environmental Instruments Inc.; the converters may be obtained from Thermo Environmental Instruments Inc., or from other converter manufacturers.

A remotely controlled manifold, 5, 5', is associated with each converter. Via respective sample lines, the manifold directs to the converter a sample from the tool, the inlet stream to the filter, the outlet stream of the filter, and the intermediate filter port, according to a sequence controlled by a computer 51. Likewise, through associated direct sample lines, unconverted samples from each port are directed to the detector 7. Within the converter, all the amines in each gas sample are converted to NO by thermal oxygenation, for example, Mixtures of airborne amines such as:

morpholine diethyleamine ethanol+$O_2$→NO+etc.

$NH_3$

NMP other amines

The converted gas and the unconverted sample air are directed to the detector 7 by air flows maintained by a vacuum pump 22 located downstream of the detector 7.

The inflow to the filtration system typically has a certain amount of $NO_x$ in it. For each sampling port, the bypass line that bypasses the converter enables the detector 7 to detect the $NO_x$ inlet value at each respective sample port in a correlated manner to the detection of the $NO_x$ value in the converted gas coming from the same ports. The difference in the $NO_x$ concentration between the two lines for a respective port yields a reading of the total amines present, by the equivalent NO value. This value is stoichiometrically related to the aggregate proton-bonding characteristic of all the amines present in the sample.

In addition to the detection of total amines, by suitable adaptations, NO and $NO_2$ concentrations in the unfiltered air are readily determined by the detector as well. For certain applications, it is desirable to know the NO and $NO_2$ present.

In another embodiment, an impinger 23 is employed to identify possible contaminants in the unconverted sample air, as shown in FIG. 3. The impinger consists of a glass or quartz tube holding a liquid. In this embodiment, vacuum pump 22 and an associated calibrated flow controller are employed to draw sample air through the liquid to take a grab sample. The grab sample is then analyzed or subjected to real-time calorimetric analysis, providing a quantitative assessment of the amine contaminants in the sample air.

Referring to FIG. 4, a filtration tower 1 is shown with a corresponding computer controlled manifold 5 and converter 6. The sampling manifold, 5, directs the specified sample to the converter while it directs a respective unconverted sample directly to the detector. Two sampling lines 20, 21 thus extend to the detector, for distances as long as, for example, 1000 feet. The length of the sampling lines is not critical because, as previously mentioned, the converted gas, NO, has a low adsorption coefficient relative to the interior surface of sampling lines, constructed, for example, of PTFE (Teflon™ of duPont) and stainless steel, whereas, in the case of the sample inlet gas, no measurement of amines is made so deposits in the sample lines are of no consequence.

In an alternate embodiment, the converter is not located near the sampling region, and silica-steel sampling lines are employed. These lines are made of stainless steel, and the inner surfaces are coated with a thin layer of fused silica. The inner surfaces are nonporous, chemically inert and have a low adsorption coefficient with respect to amines.

In the preferred embodiment, there is a heated stainless steel surface (at a temperature of 500° C. to 1000° C.) within the converter to which the sample gas is passed. This enables oxygenation with oxygen contained in the air sample. Depending upon the particular set of amines that may be expected in the installation, the precise temperature of the converter surface is determined to optimize the most efficient conversion of the amines. In other embodiments, a heated quartz surface is employed. In another embodiment a catalytic surface is provided for oxygenation to occur through catalysis, in which the surface temperature can be lower. The appropriate conversion technique is determined by the desired application, taking into account cost and conditions of use.

The $NO_x$ detector 7, or analytical module, is illustrated in FIG. 5, in conjunction with converter 6. Shown are the two sampling lines 20, 21 extending, in this case, from the converter to the detector. By action of selection valve 12, within the converter, line 20 bypasses the converter reaction unit 10 while line 21 provides converted gas to the detector. In the presently preferred implementations, the detector employs chemiluminescence for $NO_x$ detection. For this purpose NO is caused to react in the reaction chamber 30 with ozone, namely, $$NO+O_3 \rightarrow NO_2^* + O_2,$$

where the ozone is provided by an internal ozone generator 32. This produces electronically excited $NO_2$ molecules which in returning to the ground state emit photons, hv, that are detected by appropriately cooled photomultiplier 34. The reaction is given by the expression $$NO_2^* \rightarrow NO_2 + hv.$$

Associated electronics amplifies the signal from the photomultiplier (PMT) to provide a reading of $NO_x$ concentration.

The ozone reaction is conducted under conditions that prevent conversion of amines to NO, so that the $NO_x$ reading of the sample arriving unconverted from the sample port $NO_x(u)$ is not disturbed either by amines in the air sample or amines adhered to the inner surfaces of the sample conduit. Total amine detection, $A_T$, is then determined by comparison of the reading for the unconverted sample $NO_x(u)$ with the reading $NO_x(c)$ for the converted sample according to the expression $$NO_x(u) - NO_x(c) = \Delta NO_x = A_T.$$

To achieve the needed sensitivity for current deep UV photolithographic processes with presently available photomultipliers, the photomultiplier tube is cooled at least to −5° C. To achieve sensitivities required for next generation fine resolution deep UV photolithography in semiconductor manufacturing, the tube is cooled to −15° C. by associated thermoelectric cooler 36. Moreover, since there is significant variation in the sensitivity of photomultiplier tubes produced by the same manufacturer, the analyzer sensitivity is further increased by testing and choosing an optimum photomultiplier tube for the performance required. In other implementations, $NO_x$ is detected by calorimetric methods using devices available from, e.g., Tytronics, Inc. of Bedford, Mass.; other methods based upon continuous in-line sampling may also be used.

In other embodiments of the invention, additional sample lines are employed, as illustrated in FIG. 6. For instance, in an embodiment, in addition to sampling lines 20 and 21, another line is employed to direct to the detector sample gas from which amines have been removed. An unconverted sample is directed from the sampling manifold 5 to a scrubber 24. The scrubber employs chemically treated carbon filters to scrub out amines from the sample, or the amines are scrubbed out by bubbling the sample air through a liquid scrubber solution. The $NO_x$ concentration in the scrubbed sample is compared with that of the unconverted sample from sampling line 20. If the two reading are the same or within a predetermined differential threshold, the method provides further verification that the $NO_x$ readings are correct.

According to another aspect of the invention, in an instrument associated with more than one converter, each converter-detector subsystem is considered as a single instrument, which is calibrated independently of the other converter-detector subsystems. In the preferred embodiment illustrated in FIG. 1, there are two converter-detector subsystems: one subsystem serves the track and air filter system 1 and the other subsystem serves the stepper and it's air filter system 1a. For calibration purposes, zero air is provided by filter system 1 for the stepper subsystem and by filter system 1a for the track subsystem. By having the converter near the sampling area, the length of the sampling lines exposed to amines is reduced, which increases the response time of the system.

To calibrate each converter-detector subsystem, two or more samples of known concentration of contaminants are provided to the instrument, as illustrated in FIG. 7. The instrument response is then compared with the known concentrations, and a calibration curve is generated and either manually or electronically, through the software, associated with the instrument to provide corrections to the instrument's response. In general, the instrument response over the concentration range remains stable for an extended period. The instrument is sensitive, however, to zero calibration, for reasons such as drift of the PMT and the curve must be shifted relative to the true zero reading as it varies over time. Because in photolithography processing harmful contaminant concentrations are extremely low (on the order of 1 ppb or lower), in preferred systems the zero calibration is performed regularly (at least once a day) to assure the fidelity of the zero reading. In a particular preferred implementation, the detection system is arranged to operate continuously, as shown in FIG. 8, whereby the system performs a total amine detection for each of the sampling ports in turn, and conducting two calibrations each cycle, one with respect to each of the converters with which the detector operates.

In the preferred embodiment, the zero air employed for calibration is provided by the outlet ports 4 (and 4') of the filtration system (see FIG. 1). The instrument is then instructed to provide a zero reading for the calibration sample. In the case that the difference between the total amine reading for the outlet port 4 and the sample at the intermediate port 3 is not greater than zero, the sample from the outlet port 4 is employed to establish zero air. In another preferred embodiment, a sampling port located just preceding the last filter stage is employed to verify that the zero air from the output of the filter stack is in fact zero air. Also, in an alternate embodiment, a built-in dedicated zero air generator is employed. The generator provides zero air by either filtering the ambient air or by bubbling air through a liquid scrubber solution.

An external computer, preferably situated outside the clean room in which the tools are located, is employed to control the operation and monitor the entire photolithography process. The software is customized for the required application. Performance data is provided to the computer to provide an archival data base to be employed to give the contamination history of the tool clusters.

Based on the particular ports being sampled, the software employed in the operation of the instrument determines which converter-detector subsystem is to be calibrated and the appropriate source of zero air for calibration purposes. The software also designates which calibration curve to employ. As the detection system is calibrated and new zero readings are determined, the calibration curves are adjusted accordingly.

In a desired application, control instrumentation, as illustrated in FIG. 9, monitors the performance of the filtering system and the level of contamination at the track and stepper tools. Should a reading from either the stepper or track exceed a predetermined threshold, an alarm is enabled and the process is immediately shut down. However, by use of this detection system, the occurrence of such an emergency can normally be avoided.

As shown in FIG. 9, the filtering system is continuously monitored in real time as follows. The sample at the inlet to the filter system, over time, provides a quantitative history of the input of amines or other Bronstead base contaminants to the filter. By use of samples drawn from the intermediate position along the filter system as well as from the outlet of the filter stack, and measuring the difference in concentration levels from these locations, one of the following steps is caused to occur: if the difference is zero (condition green) and the total amine or Bronstead base concentration at the tool is within operating limits, then the operation continues with no interruption; when the difference is greater than zero, the difference is compared with a predetermined threshold; if the threshold is not exceeded (condition yellow), operation continues but a filter replacement is scheduled; if the threshold is exceeded, or if the total amine detected at the tool exceeds operating limits (condition red) the operation is immediately shut down.

In another embodiment, there are three or more converters remotely located at various locations in the fabrication facility. A converter is employed to monitor the general conditions in the clean room, a pair of converters is employed to monitor the contamination around a different tool cluster, and another converter is employed to monitor the contamination level within a chemical storage cabinet, to provide early indication of chemical spills.

In another implementation shown in FIG. 10, the converter-detector instrument is constructed as a mobile leak detector. The mobile unit is moved to selected regions of the fabrication facility to seek possible areas of contamination leaks. By following an escalating amine concentration trend, the mobile unit localizes the source of the contamination.

As illustrated in FIG. 11, the invention, in another preferred embodiment, is combined with a multi-point sampling system of an array of sensors to monitor the operating status of a track, including temperature, temperature of the hot plate, time on the chill plate, exposure time, etc. A total amine detector monitors process contaminants in air such as the concentration of an adhesion promoter, such as hexamethyldisilozane (HMDS), during the coating stage where photoresist is applied to the semiconductor wafers. The wafers are then sent to the stepper for exposure and subsequently brought back to the track for developing. During this stage, another, or the same, total amine detector monitors the concentration of another possibly internally processed chemical contaminant, such as tetramethylammoniumhydroxide (TMAH), employed in the developing stage.

The present invention enables, in its total amine reading, the simultaneous detection of NMP and ammonia, typically monitored previously with separate detectors. The invention enables detection, in its total amine reading of other amines that are known to be harmful to the photolithography process, such as morpholine, diethylamine ethanol, and cyclohexylamine, agents which are commonly used to inhibit corrosion in high humidity regions. Amines from the facility cafeteria, especially seafood, are also included in the detection as well as amines from the breath of the facility workers, that can create high levels of amine contamination, depending upon diet and smoking habits. As has been explained, the system as illustrated converts substantially all such air-borne amines to a common detectable compound and detects it to indicate the level of hydrogen-bonding contaminants. If high concentrations of the contaminants are detected, by grab sampling techniques, the exact sources of the contamination can be determined and remedied.

Another advantageous aspect of the invention is its adaptation to the certification process of clean rooms. Heretofore, during the certification process, each individual molecular base present in the clean room had to be detected by separate detectors. The concentrations were summed providing a number indicating the total base loading in the clean room. For instance, if three bases were present, each with a concentration of 10,000 ppt, the clean room rating would be MB30,000 (or 30,000 ppt). The present invention solves the problem of detecting individual bases by providing the total base loading within a clean room with a single reading.

In prior cases employing a chemiluminescent method of detection in other contexts, a sampling strategy and signal calculation for ammonia or total nitrogenous compounds calculation have been based on the output of two converted samples. We have recognized the importance of the fact that such strategy, if sought to be applied to the measurement of low concentrations of "total amines" for process detection, would not take into account periodic changes in the ambient NO, and $NO_2$ concentrations, and that such changes would significantly affect important readings. If the ambient NO or $NO_2$ concentrations do not vary, the ammonia or total nitrogenous compounds would be stable and supply an accurate output. However, if small variations in the ambient NO or $NO_2$ level occur, then the fidelity of the total measurement would be compromised and large variations in ambient NO or $NO_2$ level could make the signal so noisy that the data is not useful.

According to the present invention accurate chemiluminescent detection of total amines at low concentrations, for protection of the base-sensitive processes, is achievable.

The following further embodiments are particularly effective in this regard. These embodiments use an amine or process-specific (e.g., photoresist-coated) removal device or scrubber to provide, in one channel, a reference sample for non-specifically measuring "total amines" from a second channel from the same source. By removing from the reference sample substantially all of the molecules corresponding to the class of amines of interest, the reference sample may be used as a baseline for canceling the effects of background, nitrogen-containing contaminants which might contribute to the NO concentration detected by the chemiluminescent detector in the target air sample. Also, it has been determined that amine detection sensitivity improves as the operating pressure of the chemiluminescent NO concentration measurement decreases. Accordingly, the chemiluminescent NO detection is preferably carried out at sub-atmospheric pressures of 150 millibar absolute, 125 millibar absolute, or less to achieve a low noise levels and to achieve a detection sensitivity of 1 part per billion (ppb), preferably 0.5 ppb, or better.

Referring to FIG. 12, in this preferred embodiment, a sample delivery train 110 is shown for determining the total amine concentration in a sample of gas using an internal reference for zero air (i.e, amine-free air) that contains ambient $NO_x$ at the selected sampling location. The sample delivery train 110 splits each incoming sample from a sampling port 112 into two parts, channels A and B, and directs each part separately, via a three-way valve 122, to a thermal catalytic converter 124 followed by a chemiluminescent detector 126. Channel A directs part of the sample to an amine scrubber 120 and then to the three-way valve 122, while channel B directs part of the sample directly to valve 122. (The term "scrubber" as used in this document is intended to refer to any effective amine removal device, or a device that otherwise treats the amines in such a way that they have no effect on the response of the detection system being employed.)

The scrubbed and unscrubbed parts of the original sample from channel A and B, respectively, proceed from three-way valve 122 through the thermal catalytic converter 124 to the chemiluminescent detector 126 as time-separated samples in a single conduit. The difference between the response of the chemiluminescent detector 126 to samples from channel A and B equals the total amine concentration in the original sample of gas. The detector operates at a pressure of 125 millibar or less, by the co-action of vacuum pump 128 and an upstream pressure reducer 118.

Sample delivery train 110 initially takes a sample of gas from one of the sampling ports 112 and channels the sample into sample lines 116 by selection valve 114. Sample lines 116 comprising stainless steel tubes coated with fused silica (e.g., Silcosteel™) are preferred. Sample lines coated with fused silica are nonporous and nonreactive and therefore have little effect on ammonia and organic amines passing through the tubes. In contrast, commonly-used tubing of PTFE is relatively porous and tends to emit hydrogen fluoride, a strong acid, which reacts with ammonia and amines, interfering with the measurement of total amines. Silica may be deposited onto the stainless steel tubing using chemical vapor deposition. Glass tubing, steel tubing, and fiberglass tubing may also be coated with silica to reduce sample line contamination. Silica-coated sample lines 116 are used throughout sample delivery train 110 to convey the gas sample from sampling ports 112 to chemiluminescent detector 126. In certain applications, sample lines comprising glass are used. The glass sampling lines may be reinforced with epoxy.

In certain advantageous embodiments, sample lines 116 are heated substantially along their total length to approximately 50° C. using electrical heating lines (see, e.g., U.S. Pat. No. 3,727,029, incorporated herein by reference). This reduces the tendency for amines to deposit on the walls of the tubing (reduces amine-sticking coefficient) and thus reduces sample line contamination of the alternating sample gas slugs.

In this context, the combination of heating the sample lines with use of a silica coating on the lines is advantageous, though heating of sampling lines of other composition, by itself, can provide a beneficial effect. Heating is preferably accomplished using electrical resistance wire incorporated in the wall of the sample line or otherwise disposed in heat transfer relation to it.

Selection valve 114 (e.g. multi-position valve manufactured by Vici) enables samples from different locations to be channeled into a single sample delivery train 110. Following valve 114, the gas sample passes through the pressure reducer 118 (e.g., a flow restrictor, such as a capillary glass tube or a small orifice), where the pressure drops from atmospheric pressure on the upstream side of pressure reducer 118 to approximately one-tenth atmospheric pressure on the downstream side. This pressure drop is maintained by vacuum pump 128 positioned downstream of detector 126. Pressure reducer 118 preferably comprises a calibrated glass capillary heated to 50° C. to reduce the amine-sticking coefficient. The pressure reducer may be made from tubes of glass, ceramic, stainless steel, quartz, or stainless steel with an interior plated with gold or other inert material. The low pressure of the samples created by pressure reducer 118 and vacuum pump 128, in addition to enabling high sensitivity detection, reduces the response time for measuring total amine concentration. This is because the samples travel through the delivery train rapidly; for instance, in the system described, valve 122 may be shifted between channels A and B every 7 seconds in normal operation.

In other embodiments, the reference air and the target air may be sampled from different inputs. In these embodiments, it is desirable to construct channels A and B to have the same pressure drop from the input location to the converter input. Referring to FIG. 12a, separate pressure reducers 118a, 118b may be used in channels A and B. To ensure that the pressure drop in each channel is approximately the same, pressure reducer 118a in channel A contains a larger orifice than pressure reducer 118b to compensate for the affect of amine scrubber 120 on the pressure in channel A. Thus, the pressure drop between pressure reducer 118a and three-way valve 123a is equivalent to the pressure drop between pressure reducer 118b and three-way valve 123b.

The split of the gas into channels A and B occurs after the sample exits pressure reducer 118. A three-way valve 122a may be used to direct the sample into channels A and B. The amine scrubber 120 of channel A is constructed to selectively remove from the sample the totality of the multiple bases or amines to which a photolithographic or other process being guarded is sensitive, but it is constructed to not affect other nitrogen-containing compounds. Amine scrubber 120 is preferably a solid-state scrubber, comprised of an ion exchange resin with active sulfonic or carboxylic groups. The scrubber may also be comprised of any material that preferentially binds the airborne molecular bases (e.g. photoresist-coated substrates, weak acid-coated substrates, strong acid-coated substrates, ion exchange materials, or chemically treated activated carbon and molecular sieves). The properties of the active media can be chosen to optimize the selectivity of the detection process. The scrubber can be a chemical air filter medium, along the lines of the air filter that supply "zero air" in the previously described embodiments 1–10. In other embodiments of the broad aspects of the invention, the scrubber can be a wet scrubber.

A strong cation exchange resin is preferred as the scrubber substance in scrubber 120 of FIG. 12. The resin within amine scrubber 120, being a strong acid, removes multiple molecular bases, such as ammonia and other amines. A strong cation exchange resin ensures the removal of both strong and weak molecular bases, and is suitable for photoresist lithography techniques that are sensitive to both strong and weak bases. For techniques sensitive only to strong bases, a weaker acid ion exchange resin may be employed, so that weak bases are not removed and occur equally in the scrubbed and unscrubbed samples.

The sample in channel A, upon exiting amine scrubber 120, contains essentially no detrimental molecular bases, i.e., total concentration of objectionable amines is approximately zero. This amine-free sample becomes the reference sample for purposes of measuring the total amine concentration in the unscrubbed sample from channel B.

Depending upon the particular processes being monitored one or more scrubbers of a series of scrubbers may also be employed, as illustrated in FIG. 12b. These may be heated for instance to different temperatures, or contain different reactants. For adaptation of a detection system to protection of different processes, a valving and bypass system may be implemented to enable selection of the particular scrubber sections of a multi-section scrubber, for detecting the particular amines against which a respective process is being guarded.

Three-way valve 122 of FIG. 12 allows the amine-free sample from channel A and the unscrubbed sample from channel B to be directed to thermal catalytic converter 124 alternately, in rapid sequence. Operating the delivery train at 125 millibar pressure, for example, enables three-way valve 122 to switch between channel A and channel B several times per minute, to enable averaging of a number of readings, if desired, within a short monitoring interval, for instance ten minutes or less.

Thermal catalytic converter 124 (e.g., as manufactured by Thermo Environmental Instruments Inc.) converts amines in each gas sample to nitrogen oxide (NO) by thermal oxygenation. Since any given sample from channel B may contain a variety of amines (such as morpholine, diethylamine ethanol, $NH_3$, and normal methyl pyrrolidinone) thermal catalytic converter 124 must have high conversion efficiency for many types of amines. To achieve high conversion efficiency (85–100%) for a broad range of amines, a stainless steel (304 grade) surface heated to 900° C. is used within thermal catalytic converter 124. The gas sample becomes oxygenated as it passes over the heated stainless steel surface resulting in the conversion of amines to NO.

A suitable catalytic converter is diagrammatically illustrated in FIG. 12c. The converter is comprised of a reaction chamber 150 that may or may not contain a catalytic element 152 (e.g., platinum and/or palladium), a heating element 154 to heat the reaction chamber, and a thermocouple 156 connected to power control relay 158 which regulates the temperature of the reaction chamber.

The higher the efficiency of the converter, the higher the detected NO concentration signal for the same sample concentration. For this reason, a high conversion efficiency is desirable. The total amines concentration measurement is improved, however, when the conversion efficiency is substantially the same for all amines of interest. Where there are different contaminants that are converted at highest efficiency under differing conditions, a series of converters, as shown in FIG. 12d, is employed. In some preferred embodiments the converters are operated at different temperatures and/or with differing chamber designs and materials.

In some applications, gas samples entering thermal catalytic converter 124 may contain molecules that are not amines, but will nonetheless be converted into NO. For example, compounds such as $NF_3$ and HCN are not amines, yet if present in the gas sample, would be converted to NO in thermal catalytic converter 124. These compounds will not affect the total amine concentration calculation, however, because amine scrubber 120 does not retain these compounds since they are not bases. As such, samples from channel A and channel B contain equal amounts of these non-amine compounds, and thermal catalytic converter 124 converts these compounds to NO, but does so equally for channel A and channel B, thus canceling out any effect. Likewise, where the process to be monitored is sensitive only to strong bases, a scrubber is selected, e.g. a weak acid, that removes only the various strong base amines. In this case, since the weak base amines will be present in both channels, their presence does not affect the response of the system.

Converted samples exit thermal catalytic converter 124 and enter chemiluminescence detector 126 (e.g., as manufactured by Thermo Environmental Instruments Inc.). The detector 126 employs chemiluminescence for NO detection. Typically, maximum signal from chemiluminescence detector 126 is achieved at a pressure of about 65 Torr and a flow rate of 1.5 about liters per minute under the operating conditions described above. Detector 126 operates at approximately 125 millibar, suitable for detection of low amine concentrations. This high sensitivity affords detection of total amine concentrations of less than 1 ppb, preferably less than 0.5 ppb.

In the detector, NO is caused to react with ozone to produce electronically excited $NO_2$ molecules ($NO_2^*$) which in returning to ground state emit photons, hv, that are detected by a photomultiplier.

$$NO+O_3 \rightarrow NO_2^* + O_2 \quad NO_2^* \rightarrow NO_2 + hv$$

The signal from the photomultiplier is converted into time-based NO concentration values by a control system 130 and then the total amine concentration of the gas sample from the selected sampling point is determined, e.g. by appropriate averaging and differencing the values. The total amine concentration for the gas sample equals the difference between the NO concentration of the unscrubbed sample from channel B, e.g., at time $t_1$ (or the average of NO concentrations determined at times $t_1+t_3+ \ldots t_{n-1}$, n being an even number) and the NO concentration of the amine-free sample from channel A, e.g., at time $t_2$ (or the average of NO concentrations determined at times $t_2+t_4 \ldots +t_n$, n being an even number).

Additional channels may be used to provide further analysis of the components of the sampled air. For example, referring to FIG. 12e, three channels (CH1, CH2 and CH3) may be used to determine the component concentrations of NO, $NO_2$ and other non-amine nitrogen-containing compounds which are convertible to NO, and the total amines in a sampled region of air. The following discussion focuses on the nitrogen-containing compounds in the sampled air. NO, $NO_2$, amines, and other N-containing compounds reach the NO detector through CH1; and the NO detector produces a signal representative of the NO concentration in the sampled air. NO, including NO converted from $NO_2$ and other convertible N-containing molecules, and non-convertible N-containing molecules reach the NO detector through CH2; and the difference between the detector signals for CH1 and CH2 provides a measure of the concentration of $NO_2$ and other non-amine, nitrogen-containing compounds which are convertible to NO in the sampled air. NO, including NO converted from $NO_2$, amines and other convertible N-containing molecules, and non-convertible N-containing molecules reach the NO detector through CH3; and the difference between the detector signals for CH2 and CH3 provides a measure of the total amines concentration in the sampled air.

In some implementations, variations that occur in the ambient NO and $NO_2$ concentrations may affect the accuracy of the total amine concentration measurement. In such cases where the disturbance warrants, an algorithm is used to minimize the effects of such fluctuations by calculating the total amine concentration based on a moving average for NO concentrations from channel A and channel B. For example, each NO concentration measurement is added to the previous consecutive measurements and divided by the total number of measurements made at that point in time. This moving average calculation may be represented by the following algorithm.

$$\text{Moving NO Average} = (X_1+X_2+ \ldots X_n)/n,$$

where X equals the NO concentration at a given time and n equals the total number of NO measurements made. The moving average calculation may be reset periodically to avoid the weighting of out-of-date measurements. In another algorithm, a selected number of values are added together to provide an initial average value and thereafter the oldest value is dropped from the average as the newest measured valve is added to it.

Control system 130 (e.g., a computer), in addition to collecting and analyzing data received from chemiluminescence detector 126, also controls selection valve 114 and three-way valve 122. Selection valve 114 is controlled by control system 130 to channel samples from multiple sampling ports 112 into the sample delivery train 110 in a selected order. Three-way valve 122 is controlled to switch between channel A and channel B on the basis of settling times. Preferably, multiple switching cycles are employed for a given sample line and the measurements are averaged, or a running average is employed, to produce a reliable measure of total amines, as has been described.

As shown in dashed lines, for some applications a further conduit 116a may be connected to valve 122, communicating with an auxiliary vacuum pump 128a and valve 122 is modified to connect the non-selected channel A or B to the auxiliary pump. In this way substantially steady state flow conditions can be maintained in the amine scrubber, and fresh sample is immediately available to the converter 124 upon actuation of valve 122.

Referring to FIG. 13, in another embodiment, sample delivery train 110 employs an additional three-way valve 140 at the branching point downstream of pressure reducer 118. Three-way valve 140 in conjunction with three-way valve 122 isolate amine scrubber 120 and thus prevent the possibility of back-flow diffusion. Control system 130 controls the amount of sample that is directed to channel A and channel B by three-way valve 140. In a variant, shown in dashed lines, valve 140 may be connected to auxiliary vacuum pump 128b by conduit 116b so that substantially continuous flow conditions are maintained through both channels at all times.

Referring to FIG. 14, in another embodiment pressure reducer 118 is positioned downstream of thermal catalytic converter 124 and upstream of chemiluminescence detector 126. In this embodiment, amine scrubber 120 and thermal catalytic converter 124 operate at atmospheric pressure whereas chemiluminescence detector 126 operates at one-tenth atmospheric pressure.

Referring to FIG. 15, in another embodiment pressure reducer 118 is positioned downstream of amine scrubber 120 and valve 122, and upstream of thermal catalytic converter 124. In this embodiment, amine scrubber 120 operates at atmospheric pressure whereas thermal catalytic converter 124 and chemiluminescence detector 126 operate at one-tenth atmospheric pressure.

Referring to FIG. 16, in another embodiment, a separate and distinct channel for producing a reference of zero air is operated in parallel with another channel for determining the total amine concentration. Sampling point selection valves 114a and 114b, for channels 1 and 2, may be gauged and arranged to simultaneously sample the same location. Channel 1 produces a reference of zero air by directing a sample to amine scrubber 120 and then to a thermal catalytic converter 124a and a chemiluminescence detector 126a. At the same time, channel 2 directs a sample to a thermal catalytic converter 124b and a chemiluminescence detector 126b. The NO measurements from channel 1 and 2 are made simultaneously and then compared. This embodiment eliminates the effect of fluctuations in ambient NO and $NO_2$ concentrations by determining the actual NO and $NO_2$ concentration at the same time as the total NO response is being measured.

Control system 130' calculates the total amine concentration based on the differences between the two readings from detectors 126a and 126b. A calibration system (not shown) is employed to compatibly zero the instruments (e.g., to accommodate variations in the converters and detectors) so they can operate together. A correction factor based upon, e.g., computer look up of an experience table, can be employed. A calibration routine can be conducted periodically, and drift trends can be measured and stored to create a dynamic correction algorithm.

This arrangement eliminates the possibility of noise from variations in ambient NO and NO2 concentrations because the instantaneous value of the NO and NO2 concentration is always known and does not change during a calculation cycle. This system, in effect, reduces the time between ambient NO and NO2 measurements to zero, which solves the fundamental problem of fluctuations in NO and NO2 concentrations during a single calculation cycle.

The various embodiments may be implemented in a number of useful ways. The parameters of the amine scrubber are selected to remove only those amines that affect a given process. In one advantageous example, a bed of photoresist coated beads is used as the scrubber, the photoresist material being selected to correspond to the photoresist material being employed in the process being monitored. Thus the scrubber removes those amines to which the photoresist process is peculiarly sensitive. In an important case, the scrubbers used in the detection systems of FIGS. 12–16 are constructed and arranged to select construction materials for use in an amine-sensitive process (e.g. chemically amplified photoresist process). In another important case, the detection system of FIGS. 12–16 is connected to monitor the performance of an amine air filter system used to filter the air of a DUV stepper, scanner or coat/develop track. In another important case, the detection system of FIGS. 12–16 is connected to monitor the total amine concentration inside a DUV stepper, scanner, or coat/develop track. In another important case, the detection system of FIGS. 12–16 is connected to monitor cleanroom concentration of total amine concentration inside a DUV stepper, scanner, or coat/develop track. In another important case, the detection system of FIGS. 12–16 is connected to monitor the total amine concentration inside a chemical cabinet serving a DUV stepper, scanner, or coat/develop track. And in another important case, the embodiments of FIGS. 12–16 equipped as a mobile unit (see FIG. 10), or operated as an array of fixed sensing points, or a hybrid of the two systems, is used in conjunction with a search procedure for pinpointing the location of amine contamination source. For this embodiment, a series of software process steps based upon increasing and decreasing trends of concentration level, when scanning the array of values, determines the location of an amine leak (e.g., in a semiconductor process) by providing an automatic direction finder. In this case the mobile monitoring station may be automatically directed and controlled by the search algorithms to find amine leaks.

For controlling the sampling frequency of multiple sample locations in a monitoring system, an actuarial algorithm is advantageously used. On the basis of sample cost, the sampling frequencies for the various sampling points are determined in the manner that the points of greatest sensitivity and importance are monitored with greatest frequency.

In FIG. 17, a flowchart 170 of a system that performs this function is shown. The data input steps for the monitoring system include entering at step 172 the average cost of an alarm event at each sampling port 112 (i.e., the cost associated with exceeding a predetermined total amine concentration at the respective location), at step 174 or 174*a* the alarm event frequency (i.e., how frequently a sample taken from a particular sampling point will exceed a predetermined level), and at step 176 the capital costs and operating costs for the monitoring system (i.e., present value of capital and operating costs for sampling). Initially, these inputs are entered either from a database or are manually entered by a user using an input device such as a keypad connected to a computer. For instance, an alarm frequency is entered at 174*a* as determined by the software program by reference to the recorded history of alarm events at each sampling point.

Based upon the inputs, the system performs two initial calculations. At step 180, the actuarial algorithm calculates the optimum cost for the fabrication facility of sampling per hour for each sampling location, the output of which, 181, is directed to comparator 184. For step 180, Optimum sample cost/hour=(alarm event frequency)(cost of alarm event)(safety factor), where the alarm event frequency equals the number of alarms per hour, and the cost of alarm event equals the dollar cost per alarm event. A safety factor (e.g., 2) may be used to decrease the probability that an alarm event will occur due to failure of the detection sequence.

At step 182, the actual equipment cost of sampling per hour is determined based on the capital and operating expenses for the monitoring system, its output, 183, is also directed to comparator 184. For step 182, Actual equipment cost/hour=[(capital costs/hour)+(operating costs/hr)]/(number of sampling locations).

Next, the output 181 from step 180 (i.e., optimum sample cost) and the output 183 of step 182 (i.e., actual equipment cost) are compared at step 184 to determine whether the frequency of sampling from each location should be modified. If the optimum sample cost is greater than the actual equipment cost, step 186 determines that the sampling frequency should be increased. Likewise, if the optimum sample cost is less than the actual equipment cost, a determination is made that the sampling frequency should be decreased.

Based on the information provided at step 186, the sample frequency is changed at step 188 or 188*a*. The optimum sampling frequency is input at step 188 into the control system 130, while provision is made, step 188*a*, for manually changing sample frequency in accordance with the determination of the program. An optimum sampling frequency for each sampling port is calculated according to the following formula:

Optimum sampling frequency=(optimum sample cost/hr)(equipment sample frequency/actual equipment cost), where the equipment sample frequency equals the number of samples the monitoring system can process per hour divided by the number of sampling ports. FIG. 18 is a table providing examples of the calculations previously mentioned for a hypothetical monitoring system using seven sampling locations.

Referring to FIG. 19, in another embodiment, a flowchart 203 of a system that optimizes sample frequency based upon past performance is shown. At step 201 the concentration history at each sampling location 112 is entered into the memory of a multi-channel base contaminant monitor 200. Step 202 calculates and records the frequency with which a given sampling location exceeds a predetermined level. The frequency data for each sampling location then become inputs 204 into optimum sample frequency calculation step 206. The sample sequencing is adjusted at step 208 in accordance with stored optimization criteria data which, for example, is weighted according to the cost of alarm events at the respective sampling locations. The monitor is also structured to determine a sampling sequence for new channels which have similar characteristics to the existing channels. The sample frequency optimization improves monitoring efficiency by adjusting sample frequency based upon empirical evidence.

Referring to FIG. 20, in another embodiment, the multichannel base contaminant monitor 210 calculates the sequence of channel monitoring based upon the similarity of the average concentration of contaminants measured at the various sampling points. At step 212 the concentration history at each sampling location 112 is entered into the memory of monitor 210. Step 216 calculates the average concentration measured at each sampling location. These averages then become inputs 218 into sample frequency calculation step 220. The sample sequencing is adjusted at step 222 based on the grouping of channels with similar average concentration measurements.

For example, if channels 1, 4, and 5 always return a concentration of between 1–3 parts per billion (ppb) and channels 2, 3, and 6 always return a concentration of between 80–100 ppb, the system is constructed to automatically change the sampling sequence such that channels 1, 4, and 5 are sampled in sequence and channels 2, 3, and 6 are similarly sampled. By grouping similar channels, the system decreases the average amount of time the instrument needs to stabilize between channels, thereby increasing the number of samples the instrument can handle over a given time.

Certain broad aspects of the invention can be realized in other ways. For instance the total amine detector may be based on wet chemistry instead of thermal conversion. The common compound to which multiple base contaminants may be thermally converted may be a compound other than NO.

Detection techniques different from chemiluminescence can be employed, etc.

What is claimed is:

1. A detection system for detecting base contamination in a semiconductor processing system comprising;
    a converter system that oxygenates amines contained in received gas samples;
    a sample line that deliver s gas sample s to the converter system;
    a detector system coupled to the converter system that receives converted gas samples from the converter system, the detector system producing signals representative of the oxygenated amine concentration contained in converted gas samples.

2. The detection system of claim 1, further comprising first and second sample lines coupled to a converter system and a common detector system.

3. The detection system of claim 1, wherein the detector system is coupled to the converter system.

4. The detection system of claim 1, further comprising a vacuum pump coupled to the detector system.

5. The detection system of claim 1, wherein the converter system convert s multiple amines in a gas into a detectable compound, and the detector system detect s the detectable compound produced by the converter system.

6. The detection system of claim 1, wherein the converter system is adapted to oxygenate multiple amines into NO.

7. The detection system of claim 1, wherein the detector system is a chemiluminescent NO detector.

8. The detection system of claim 1, further comprising an amines remover.

9. The detection system of claim 8, wherein the amines remover comprises a liquid scrubber solution or a chemical filter.

10. The detection system of claim 1, further comprising a valve for alternately connecting first and second sample liens to the converter system.

11. The detection system of claim 1, wherein the converter system includes a plurality of converter systems and the detector system includes a single detector, and further comprising valving for alternatively connecting the converter systems to the detector.

12. The detection system of claim 11, wherein the detector system includes a calibration system that provides calibration valves for the detector.

13. The detection system of claim 12, including a separate source of zero air for calibrating each respective subsystem.

14. The detection system of claim 1 combined with a photolithographic semiconductor production system.

15. The combination of claim 14 connected to monitor air at a stepper of the production system.

16. The combination of claim 15 connected to monitor air at a coat and develop photolithography track of the production system.

17. The combination of claim 14 connected to monitor remaining filter life of an air filter system supplying air to said production system and contaminant concentrations at a stepper and coat and develop track of said production system.

18. The detection system of claim 1 adapted to monitor air quality for an environment of a deep UV photolithography process, the system having a sensitivity of 1 ppb or better for amine contaminants.

19. The detection system of claim 18 in which the detection system includes a photomultiplier tube, and a cooler is arranged to cool the tube to achieve an amines sensitivity of at least about 1 ppb.

20. The detection system of claim 1 connected to monitor the total amine concentration at selected stages of a multistage manufacturing process.

21. The detection system of claim 20 connected to monitor the total amine concentration of a coat and develop track tool in a deep UV photolithography process.

22. The detection system of claim 1, wherein first and second sample lines have an interior surface with a low adsorption coefficient for amines.

23. The detection system of claim 22 wherein each of the first and second sample lines has an interior surface comprising silica.

24. The detection system of claim 23, wherein the sample lines comprise stainless steel tubing coated with silica.

25. The detection system of claim 23, wherein the sample lines comprise glass tubing.

26. The detection system of claim 25, wherein the glass tubing is coated with silica.

27. The detection system of claim 25, wherein the glass tubing is reinforced with epoxy.

28. The detection system of claim 22 wherein the detector system determines the concentration of amines based upon a detector system signal produced from a gas sample received from the first sample line and a detector system signal produced for a gas sample received from the second sample line.

29. The detection system of claim 1, further comprising a pressure reducer located upstream of the detector system and a pump located downstream of the detector system.

30. The detection system of claim 29, wherein the pressure reducer comprises a calibrated glass capillary heated to reduce the amine-sticking coefficient.

31. The detection system of claim 29, wherein the pressure reducer is located upstream of the converter system.

32. The detection system of claim 29, wherein the pressure reducer is located upstream of the amines remover.

33. The system of claim 1, wherein the amines remover comprises photoresist coated beads.

34. The detection system of claim 1, further comprising a control system operable to implement a process for lowering the amplitude of calculation errors caused by intra calculation cycle concentration variations of NO and $NO_2$.

35. The detection system of claim 34, wherein the process is based on a moving average.

36. The detection system of claim 35, wherein the moving average is selected to smooth the noise in the measurement in a manner that diminishes over-time as the number of averaging cycles increases.

37. The detection system of claim 34, wherein the control system is operable to implement an actuarial process that controls the sampling frequency of multiple sample locations in a monitoring system based on sample cost, such that the points of greatest sensitivity and importance are monitored with greatest frequency.

38. The detection system of claim 34, wherein the control system is operable to implement a series of processes for determining the location of an amine leak by providing an automatic direction finder based upon increasing pollutant concentrations.

39. The detection system of claim 34, wherein the control system is operable to implement a series of processes for controlling a multi-channel base contaminant monitor by determining a sampling strategy for the channels based on the frequency with which the channels exceed a predetermined level.

40. The detection system of claim 34, wherein the control system is operable to implement a series of processes for controlling a multi-channel base contaminant monitor by determining a sampling strategy for new channels based on the frequency with which existing channels exceed a predetermined level.

41. The detection system of claim 34, wherein the control system is operable to implement a series of processes for controlling a multi-channel base contaminant monitor which calculates the sequence of channel monitoring based upon the similarity of the average concentration of contaminants measured.

42. The detection system of claim 8, wherein the amines remover and the converter system are located proximal to a sampling point and the detection system is located remotely from the sampling point.

43. A detection system configured to monitor molecular amine contamination in sampled air by implementing the following steps:

sampling air from a region;

converting amines contained in sampled air into NO to provide a target air sample;

removing amines from sampled air to provide a scrubbed air sample;

converting amines contained in the scrubbed air sample into NO to provide a reference air sample;

determining by chemiluminescence the NO concentrations in the reference air sample and in the target air sample; and determining a total amine concentration from the difference between the determined NO concentrations in the target air sample and in the reference air sample.

44. The system of claim 43, wherein the NO concentrations in the reference air sample and in the target air sample are both determined within the same ten-minute period of time.

45. The system of claim 43, wherein the NO concentrations in the reference air sample and in the target air sample are determined at substantially the same time.

* * * * *